United States Patent [19]

Muchowski et al.

[11] Patent Number: 4,560,699
[45] Date of Patent: Dec. 24, 1985

[54] 5-(4-VINYLBENZOYL)-1,2-DIHYDRO-3H-PYRROLO-[1,2-A]-PYRROLE-1-CARBOXYLIC ACIDS AND DERIVATIVES THEREOF AND USE AS ANALGESICS AND ANTI-INFLAMMATORIES

[75] Inventors: Joseph M. Muchowski, Sunnyvale; Stefan H. Unger, Palo Alto, both of Calif.

[73] Assignee: Syntex (U.S.A.) Inc., Palo Alto, Calif.

[21] Appl. No.: 458,243

[22] Filed: Jan. 17, 1983

[51] Int. Cl.$^4$ .................... A61K 31/40; C07D 487/06
[52] U.S. Cl. .................................. 514/413; 548/453
[58] Field of Search .................. 548/453; 424/274; 514/413

[56] References Cited

U.S. PATENT DOCUMENTS 4,089,969 5/1978 Muchowski et al. ............. 548/453

FOREIGN PATENT DOCUMENTS 2027025 2/1980 United Kingdom .............. 424/277

Primary Examiner—Glennon H. Hollrah
Assistant Examiner—D. B. Springer
Attorney, Agent, or Firm—Ellen J. Buckles; Tom M. Moran; Alan M. Krubiner

[57] ABSTRACT

Novel 5-(4-vinyl- or 4-ethynylbenzoyl)-1,2-dihydro-3H-pyrrolo[1,2-a]pyrrole-1-carboxylic acids represented by the formula

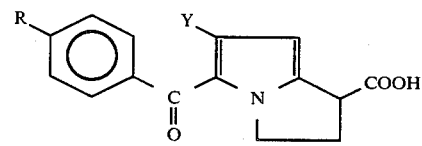

and the pharmaceutically acceptable, non-toxic alkyl esters and salts thereof, wherein R is vinyl or ethynyl, and Y is hydrogen, a lower alkyl group having from 1 to 6 carbon atoms, chloro or bromo.

5 Claims, No Drawings

5-(4-VINYLBENZOYL)-1,2-DIHYDRO-3H-PYRROLO-[1,2-A]-PYRROLE-1-CARBOXYLIC ACIDS AND DERIVATIVES THEREOF AND USE AS ANALGESICS AND ANTI-INFLAMMATORIES

BACKGROUND OF THE INVENTION

1. Field of the Invention

This invention relates to (i) 5-(4-vinyl- or 4-ethynyl-benzoyl)-1,2-dihydro-3H-pyrrolo[1,2-a]pyrrole-1-carboxylic acids and the pharmaceutically acceptable, non-toxic alkyl esters and salts thereof; (ii) the use of these compounds as anti-inflammatory agents, analgesic agents, platelet aggregation inhibitors, fibrinolytic agents and smooth muscle relaxants (this includes both prophylactic and therapeutic use); (iii) pharmaceutical compositions comprising a compound of this invention and at least one pharmaceutical excipient; and (iv) processes for preparing the compounds of this invention.

2. Related Art

Compounds are known which are represented by the formula

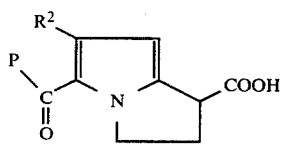

wherein P is a moiety selected from the group consisting of

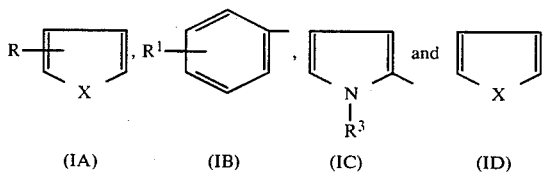

in which

X is oxygen or sulfur,

R is hydrogen, methyl, chloro or bromo, the R substitution being at the 3, 4 or 5 positions of the thiophene ring, $R^1$ is hydrogen, a lower alkyl group having 1 to 4 carbon atoms, a lower alkoxy group having from 1 to 4 carbon atoms, chloro, fluoro or bromo, the $R^1$ substitution being at the ortho, meta or para positions of the phenyl group, and $R^2$ is hydrogen, lower alkyl having from 1 to 4 carbon atoms, chloro, bromo, lower alkylthio, lower alkyl sulfinyl or lower alkyl sulfonyl, and $R^3$ is hydrogen or a lower alkyl group having from 1 to 4 carbon atoms.

The compounds represented by Formula (IA) and (ID) are disclosed in U.S. Pat. No. 4,087,539, issued May 2, 1978 to Muchowski et al, while compounds of Formulas (IB) and (IC) are disclosed in U.S. Pat. No. 4,089,969, issued May 16, 1978 to Muchowski et al and U.S. Pat. No. 4,097,579 issued June 27, 1978 to Muchowski et al, respectively.

Compounds of Formula (IB) wherein $R^1$ is methylsulfinyl or methylsulfonyl are disclosed in U.S. Pat. No. 4,232,038, issued Nov. 4, 1980. Compounds of Formula (IB) wherein $R^2$ is chloro or bromo are disclosed in U.S. Pat. No. 4,344,943, issued Aug. 17, 1982. Compounds of Formulas IB and ID wherein $R^2$ is lower alkylthio, lower alkylsulfinyl, or lower alkylsulfonyl, are described in copending U.S. application Ser. No. 386,174, filed June 8, 1982. All of these compounds are useful as anti-inflammatory agents, analgesic agents, platelet aggregation inhibitors, fibrinolytic agents and smooth muscle relaxants. They can be used both prophylactically and therapeutically.

SUMMARY

The invention herein concerns, in one aspect, the novel compounds represented by the formula

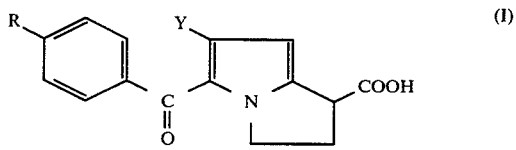

and the pharmaceutically acceptable, non-toxic alkyl esters having from 1 to 12 carbon atoms and the pharmaceutically acceptable salts thereof, wherein R is vinyl or ethynyl, and Y is hydrogen, a lower alkyl having from 1 to 6 carbon atoms, chloro or bromo.

In a second aspect, this invention relates to a pharmaceutically composition comprising a pharmaceutically acceptable excipient and at least one compound represented by Formula I.

A third aspect of the invention concerns methods of using compounds of Formula I, or pharmaceutical compositions containing them, as anti-inflammatory agents, analgesic agents, antipyretic agents, vasospasm inhibitors, platelet aggregation inhibitors, fibrinolytic agents and smooth muscle relaxants.

A fourth aspect of the invention concerns a process for the preparation of compounds of Formula I, and the pharmaceutically acceptable non-toxic esters and salts thereof.

DETAILED DESCRIPTION OF THE INVENTION

Definitions

As used herein:

"Lower alkyl" means a branched or unbranched hydrocarbon chain containing 1 to 6 carbon atoms, or the number of carbons specified, including but not limited to methyl, ethyl, propyl, isopropyl, n-propyl, butyl, i-butyl, pentyl and the like.

"Pharmaceutically acceptable, non-toxic alkyl esters and pharmaceutically acceptable salts" refers to alkyl esters derived from branched or straight chain hydrocarbons having from one to twelve carbon atoms and pharmaceutically acceptable salts derived from inorganic and organic bases, respectively.

Typical pharmaceutically acceptable, non-toxic alkyl ester groups are, for example, methyl, ethyl, propyl, isopropyl, butyl, t-butyl, isoamyl, pentyl, isopentyl, hexyl, octyl, nonyl, isodecyl, 6-methyldecyl and dodecyl esters.

Pharmaceutically acceptable, non-toxic salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary, and tertiary amines and substituted amines including naturally occurring substituted amines, cyclic amines and basic ion exchange resins. Such salts are exemplified by, for example, isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

In naming the compounds of this invention IUPAC nomenclature is used. The compounds of this invention are named as 1-carboxylic acids using the numbering system set forth in the "Abstract of the Disclosure." For example, the compound of Formula I where R is vinyl and Y is chloro is named 5-(4-vinylbenzoyl)-6-chloro-1,2-dihydro-3H-pyrrolo[1,2-a]-pyrrole-1-carboxylic acid. The methyl ester of that compound is named methyl 5-(4-vinylbenzoyl)-6-chloro-1,2-dihydro-2H-pyrrolo[1,2-a]-pyrrole-1-carboxylate.

The novel compounds of Formula I depicted below exist as pairs of optical isomers (or enantiomorphs), i.e., a (dl) mixture. Each optical isomer as well as the (dl) mixtures thereof are included within the present invention.

A preferred group of compounds are the compounds of Formula I wherein Y is hydrogen, and the pharmaceutically acceptable esters and salts thereof.

The (d)-acid isomer of Formula I and the pharmaceutically acceptable esters and salts thereof are useful as intermediates for the preparation of the (dl)-acid of Formula I, as described more fully below.

Process of Preparation

The novel (dl) compounds of the present invention represented by Formula I are prepared by a process illustrated by Reaction Sequence 1 as follows:

REACTION SEQUENCE 1

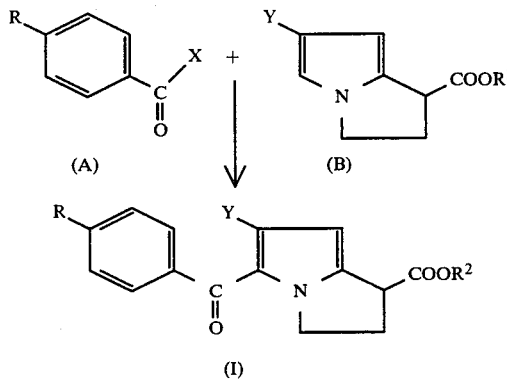

in which X is Cl, Br or NR³R⁴, wherein R³ and R⁴ are independently lower alkyl, cycloalkyl, or morpholino, R² is lower alkyl and R and Y are as defined hereinabove. In the reaction shown above, the compounds of Formula I are synthesized by acylation of the pyrolopyrrole (B) with the acid halide or the dialkylamide derivative of the compound of Formula A.

The compounds of Formula A are known and are either readily commercially available, or can be prepared by means well known in the art. For example, a method of synthesis of 4-vinylbenzoic acid is described in *J. Chem. Education*, 55, 813 (1978), and a method of synthesis of 4-ethynlbenzoic acid is described in *J. Org. Chem.*, 43, 4987 (1978).

The compounds of Formula B are disclosed in the above-cited patent references and can be prepared by several alternate synthetic procedures, two of which are described hereinbelow. The choice of an appropriate synthetic route to obtaining the compound of Formula B will depend upon whether Y is a hydrogen, lower alkyl, or halide.

Preparation of compounds of Formula B in which Y is hydrogen or lower alkyl

The starting compounds of Formula B in which Y is either hydrogen or a lower alkyl group can be prepared by a process illustrated by Reaction Sequence II as follows:

REACTION SEQUENCE II

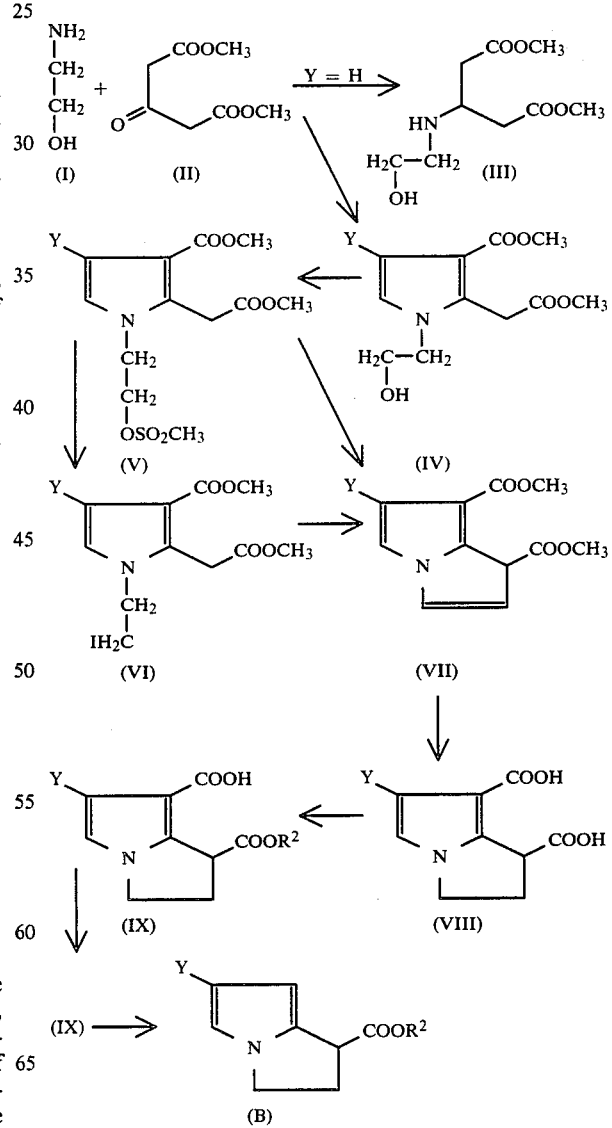

wherein R² is a lower alkyl group of 1 to 4 carbon atoms, e.g., methyl, ethyl, propyl, isopropyl and n-butyl.

In practicing the process outlined above, for the preparation of the compound of Formula (IV) wherein Y is hydrogen, equimolecular amounts of ethanolarose (I) and dimethyl 1,3-acetonedicarboxylate (II) are reacted at a temperature of from about 0° to about room temperature, to readily form a solution of the vinylamine of Formula (III), which is then treated, preferably in situ, in a suitable inert organic solvent, under anhydrous conditions, with 2-bromoacetaldehyde or 2-chloroacetaldehyde, at from about 40° to about 100° C. for a period of time of from about 30 minutes to about 16 hours. Suitable solvents for this reaction are the aprotic solvents such as acetonitrile, tetrahydrofuran, dimethoxyethane, chloroform, dichloromethane and the like. In the preferred embodiments, the reaction is conducted in acetonitrile solution, at reflux temperature for about 1 hour. The 2-bromo-(chloro)-acetaldehyde reagents are known compounds, or can be obtained by pyrolysis of the corresponding diethyl acetals in the presence of oxalic acid dihydrate.

To prepare the compounds of Formula (IV) wherein Y is a lower alkyl group, preferably straight chain, having 1 to 4 carbon atoms, an aqueous mixture of ethanolamine (I) and dimethyl 1,3-acetonedicarboxylate (II) is treated with a compound of the formula R³—CO—CH₂X, wherein X is bromo or chloro and R³ is a lower alkyl group, preferably straight chain, of from 1 to 6 carbon atoms, and most preferably 1-bromoacetone, 1-bromo-2-butanone, 1-bromo-2-pentanone, and 1-bromo-2-hexanone, at from about 40° to about 100° C. for a period of time from about 30 minutes to about 16 hours. In the preferred embodiment the reaction is conducted at a temperature of from about −10° C. to about room temperature for from about 1 hour to about 6 hours. The R³—CO—CH₂X reagents are known compounds.

Esterification of compound (IV) with methanesulfonyl chloride in the presence of a tertiary amine, i.e., triethylamine, pyridine and the like, optionally in the presence of a co-solvent such a dichloromethane, at a temperature of from about −10° C. to about room temperature, for about 10 minutes to about 2 hours produces the corresponding mesylate of Formula (V), which is converted into the corresponding N-(2-iodoethyl)pyrrole of Formula (VI) by reaction with sodium iodide in acetonitrile solution, at reflux temperature for from about one to about ten hours.

Upon reaction of the iodoethyl compounds of Formula (VI) with sodium hydride in a suitable inert organic solvent such as dimethylformamide there are obtained dimethyl 1,2-dihydro-3H-pyrrolo[1,2-a]-pyrrole-1,7-dicarboxylate and the 6-alkyl substituted derivatives thereof (VII). This cyclization is conducted under an inert atmosphere, i.e., under argon or nitrogen atmosphere, at temperatures of the order of from about 15° to about 40° C., for a period of time of from about 15 minutes to about 4 hours. Best results, when Y is hydrogen, are obtained conducting the reaction at room temperature, for about 30 minutes.

Alternatively, the compounds of Formula (VII) can be prepared by direct cyclization of the mesylate (V), with sodium hydride in dimethylformamide solution, at from about −10° C. to about room temperature, for from about 30 minutes to about 2 hours.

Basic hydrolysis of a compound of Formula (VII) with an alkali metal hydroxide or alkali metal carbonate, e.g., sodium hydroxide, potassium hydroxide, sodium carbonate, potassium carbonate and the like in an aqueous lower aliphatic alcohol, e.g., methanol or ethanol, at a temperature of between room temperature and reflux, for from about 4 to about 24 hours, affords the corresponding free diacid of Formula (VII), i.e., 1,2-dihydro-3H-pyrrolo[1,2-a]pyrrole-1,7-dicarboxylic acid and the 6-alkyl derivatives thereof. The hydrolysis is preferably carried out using aqueous methanolic potassium hydroxide at reflux temperature for about 10 hours.

The carboxylic acid group at the C-1 position in compound (VIII) is then selectively esterified by treatment with a lower aliphatic alcohol, e.g., methanol, ehtanol, isopropanol, n-butanol and the like in the presence of hydrogen chloride, to produce the corresponding alkyl 1,2-dihydro-3H-pyrrolo[1,2-a]pyrrole-1-carboxylate-7-carboxylic acid of Formula (IX). The reaction is conducted at a temperature of from about 0° to about 50° C. for about 1 hour to 4 hours.

Decarboxylation of the monoesterified compounds (IX) to the corresponding compounds of Formula (B), the key intermediates in the process for obtaining the compounds of the present invention, is achieved by heating (IX) at an elevated temperature, of the order of from about 230° to about 280° C., for a period of time sufficient to complete the reaction. The course of the reaction can be followed by the rate of carbon dioxide evolution and t.l.c. analysis, decarboxylation being generally completed within from about 45 to about 90 minutes. The reaction product, namely, alkyl 1,2-dihydro-3H-pyrrolo[1,2-a]pyrrole-1-carboxylate and the 6-alkyl derivatives thereof (B) can be purified by chromatographic techniques. Alternatively, and particularly for the decarboxylation of small batches of compound (IX), the reaction product (B) can be distilled directly from the reaction vessel.

Preparation of compounds of Formula B in which Y is chloro or bromo

The compounds of Formula B in which Y is either chloro or bromo can be prepared by a process illustrated by Reaction Sequence III as follows:

REACTION SEQUENCE III

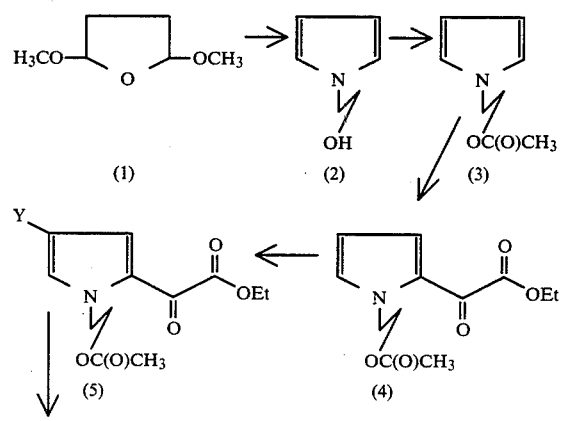

-continued
REACTION SEQUENCE III

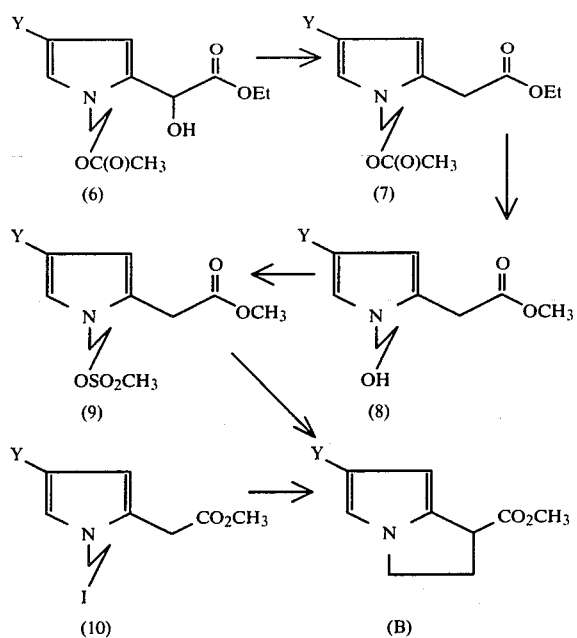

In practicing the process outlined above, in the first step in the preparation of the compound represented by Formula (2), 2,5-dimethoxytetrahydrofuran (1) is reacted with ethanolamine in an organic acid. Generally the reaction is carried out with a 2 to about 10 times molar access of the ethanolamine over the dimethoxytetrahydrofuran with the reaction taking place in a substantial excess of the organic acid, preferably acetic acid. The reaction will take place at a temperature of about 50° to 125° C., preferably at about 110° to 120° C. or the boiling point of the reaction mixture. The reaction is completed within 5 to about 20 hours and generally will be completed in less than 10 hours at temperatures between 115° and 120° C. The reaction can be carried out in a continuous or a batch mode, preferably the latter.

Once the 1-(2-hydroxyethyl)pyrrole is obtained, it is esterified by any suitable means known in the art. For example, acetic acid is reacted with the 1-(2-hydroxyethyl)pyrrole in the presence of a strong acid such as sulfuric acid, and the reaction mixture is heated sufficiently to distill off the water that is formed as a result of the reaction. Preferably however, the pyrrole is reacted with acetyl chloride or acetic anhydride in a suitable solvent wherein there is a molar excess of the acetyl chloride or acetic anhydride. This reaction takes place at room temperature and will be completed in a relatively short period of time, with only an hour or two at the most being required for the reaction to reach completion. The 1-(2-acetoxyethyl)pyrrole is then isolated and purified by any means known in the art, such as extraction with a suitable organic solvent and removal of the solvent, to yield the desired compound represented by Formula (3).

In the next step, a solution of pyridine in anhydrous dichloromethane is added to a stirred and cooled solution of ethoxyalyl chloride in anhydrous dichloromethane so that the reaction temperature remains at about −20° to −25° C. Upon completion of this addition an approximately equimolar amount of 1-(2-acetoxyethyl)-pyrrole of Formula (3) in anhydrous dichloromethane is added while the temperature is maintained at about −20° to 0° C. Washing with water, drying, removal of the solvent and purification gives ethyl 1-(2-acetoxyethyl)pyrrole-2-glyoxylate.

Once the glyoxylate of Formula (4) is obtained, it is chlorinated or brominated using a suitable chlorinating or brominating agent. To increase selectivity, the reaction is effected at low temperatures. Thus, the glyoxylate of Formula (4) is cooled to −50° C., preferably to about −70° C., after dissolving in an inert anhydrous halogenated alkane solvent such as dichloromethane. A suitable chlorinating agent is sulfuryl chloride while a suitable brominating agent is bromine. The reaction mixture, after the addition of the chlorinating or brominating agent is complete, is allowed to warm up to ambient temperature, whereupon the organic solvent is removed. Generally the reaction takes no longer to complete than the time required to add the chlorinating or brominating agent. The 4-chloro or 4-bromopyrrole thus formed is readily separated from other related compounds by suitable means known in the art, such as thin layer chromatography, column chromatography, gas-liquid chromatography (GLC) or high pressure liquid chromatography (HPLC).

The 4-chloro or 4-bromoglyoxylate of Formula (5) is then reduced to the corresponding ethyl 1-(2-acetoxyethyl)-pyrrole-2-glycolate. This selective reduction of the 1-keto group is achieved by using a reducing agent such as an alkali metal borohydride (for example potassium borohydride or, preferably sodium borohydride) in a methanol/water solution. The reaction takes place at temperatures of −10° to about −60° C., preferably about −30° C. if Y is chloro and −50° C. if Y is bromo.

In the next step, iodine is dissolved in a dry, aromatic hydrocarbon solvent, such as benzene, and triphenylphosphene is added under an inert atmosphere (e.g. argon). The α-hydroxyacetate is then added to this mixture and reacted for a period of time sufficient to eliminate the 1-hydroxy group. Where Y is chloro, the reaction mixture will generally be reacted for less than about 5 hours and usually will require about 2½ hours at reflux temperatures. The resulting compound of Formula (7) is then isolated using methods well known in the art.

Once the compound of Formula (7) is obtained, it is converted to the corresponding methyl 1-(2-hydroxyethyl)-4-chloro or 4-bromopyrrole-2-acetate. The conversion is accomplished by dissolving the compound of Formula (7) in anhydrous methanol and adding a suitable amount of 1,5-diazabicyclo[4.3.0]non-5-ene (DBN). Generally the reaction takes place at room temperature under an inert atmosphere (nitrogen) and is completed in less than about 20 hours, generally about 6 hours for the 4-chloro compound and about 18 hours for the 4-bromo compound. After suitable isolation and purification one obtains a compound of Formula (8), namely methyl 1-(2-hydroxyethyl)-4-chloro or 4-bromopyrrole-2-acetate.

Esterification of the compound of Formula (8) produces the corresponding mesylate of Formula (9). The compound of Formula (8) is reacted with methanesulfonyl chloride in the presence of a tertiary amine, i.e., triethylamine, pyridine and the like, optionally in the presence of a co-solvent such as dichloromethane, at a temperature of from about −10° C. to about room temperature, for about 10 minutes to about 2 hours. The resulting mesylate of Formula (9) is in turn converted to the corresponding N-(3-iodoethyl)pyrrole of Formula (10) by reaction with sodium iodide in acetonitrile solution at reflux temperature for from about one to about ten hours.

Upon reaction of the iodoethylpyrrole of Formula (10) with sodium hydride in a suitable inert organic solvent such as dimethylformamide there is obtained a compound of Formula (B), namely methyl-1,2-dihydro-3H-6-chloro or 6-bromopyrrolo[1,2-a]pyrrole-1-carboxylate. This cyclization is conducted under an inert atmosphere, i.e., under argon or nitrogen atmosphere, at temperatures of about 15° to about 40° C., for a period of about 15 minutes to about 4 hours. Best results are obtained conducting the reaction at room temperature for about 30 minutes.

Alternatively, the compounds of Formula (B) can be prepared by direct cyclization of the mesylate (9), with sodium hydride in dimethylformamide solution, at from about −10° C. to about room temperature, for from about 30 minutes to about 2 hours.

Preparation of the compounds of Formula I

The novel compounds of this invention, as represented by Formula I, are prepared from the appropriately substituted pyrole-pyrrole derivative of Formula (B) by acylation with the acid halide or dialkyalamide compounds of Formula (A), as illustrated by Reaction Sequence III:

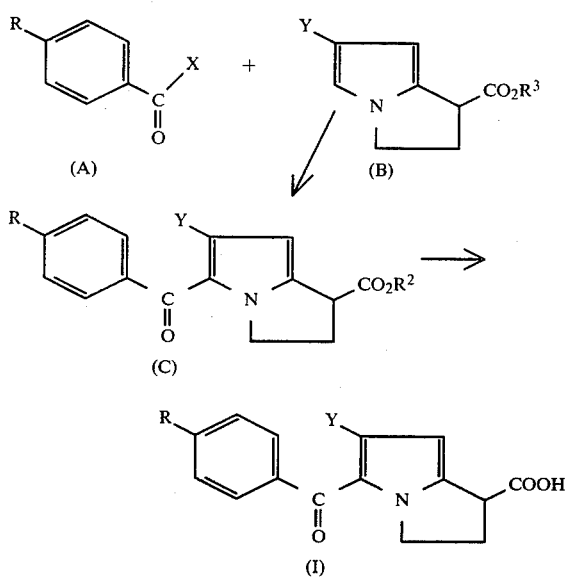

Condensation of a compound of Formula (B) with an amide of Formula (A), affords the corresponding alkyl 5-benzoyl-1,2-dihydro-3H-pyrrolo[1,2-a]pyrrole-1carboxylate (C). This reaction is conducted in an inert organic aprotic solvent in the presence of phosphorous oxychloride, at reflux temperature, for from about 1 to about 175 hours, under an inert atmosphere, followed by further reflux in the presence of sodium acetate, for from about 2 to about 10 hours. Other acid chlorides such as phosgene or oxalyl chloride may be substituted for the phosphorous oxychloride.

In the preferred embodiments, this condensation is carried out by adding a solution of compound (B) in a suitable solvent to a previously refluxed mixture of 1.1 to 5 molar equivalents of both the desired amide and phosphorous oxychloride in the same solvent, refluxing the reaction mixture thus obtained for from about 6 to about 72 hours under an argon atmosphere and thereafter adding thereto from about 3 to about 10 molar equivalents of sodium acetate, followed by an additional reflux period for from about 4 to about 6 hours.

Adequate solvents for this reaction are the halogenated hydrocarbons such as dichloromethane, 1,2-dichloroethane, chloroform, carbon tetrachloride and the like, dimethoxyethane and tetrahydrofuran. The preferred solvent is 1,2-dichloroethane.

Representative of the N,N-dimethyl arylamides which can be used are:
N,N-dimethyl-4-vinylbenzamide;
N,N-dimethyl-4-ethynylbenzamide;
N,N-diethyl-4-vinylbenzamide; and
N,N-diethyl-4-vinylbenzamide.

These amides are known compounds and can be prepared in a conventional manner from the corresponding acids i.e., by conversion into the acid chlorides followed by treatment with dimethylamine.

Alternatively a compound represented by Formula (C) may be prepared by condensing a compound of Formula (B) with the acid chloride or acid bromide of formula (A). This reaction is carried out in an inert atmosphere (e.g. argon) and a suitable inert hydrocarbon solvent such as xylene. Suitable acid halides are those which correspond to N,N-dimethylarylamides set forth hereinbefore:
4-vinylbenzoyl chloride;
4-ethynylbenzoyl chloride;
4-vinylbenzoyl bromide; and
4-ethynylbenzoyl bromide.

These acid chlorides are known compounds and can be prepared in a conventional manner from the corresponding acids. Methods of preparing the 4-vinylbenzoyl and 4-ethynylbenzoyl chlorides are given in J. Chem. Education, 55, 813 (1978) and in J. Org. Chem., 43, 4987 (1978) respectively, and can readily be applied to preparation of the corresponding bromide compounds.

Upon alkaline hydrolysis of the alkyl ester group in a compound of Formula (C) there is obtained the corresponding free acid of Formula (I). This hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 15 minutes to about 2 hours, under an inert atmosphere. Preferably, this hydrolysis is effected with aqueous methanolic potassium carbonate, at reflux temperature for about 30 minutes.

The compounds of Formula (I) are obtained from the above procedure as racemic (d,l) mixtures, and can be resolved by any of several suitable methods known in the art, to obtain the corresponding individual isomers therof. For example, the (l)-acid isomers and (d)-acid isomers of the compounds of Formula (I) can be obtained by applying the known technique of high pressure liquid chromotography (HPLC) to the α-phenethyl diastereoisomeric esters of the compounds of Formula (I), followed by acid cleavage. Thus, for example, the compounds of Formula (I) wherein Y is hydrogen can be subjected to further treatment in accordance with the following flow diagram:

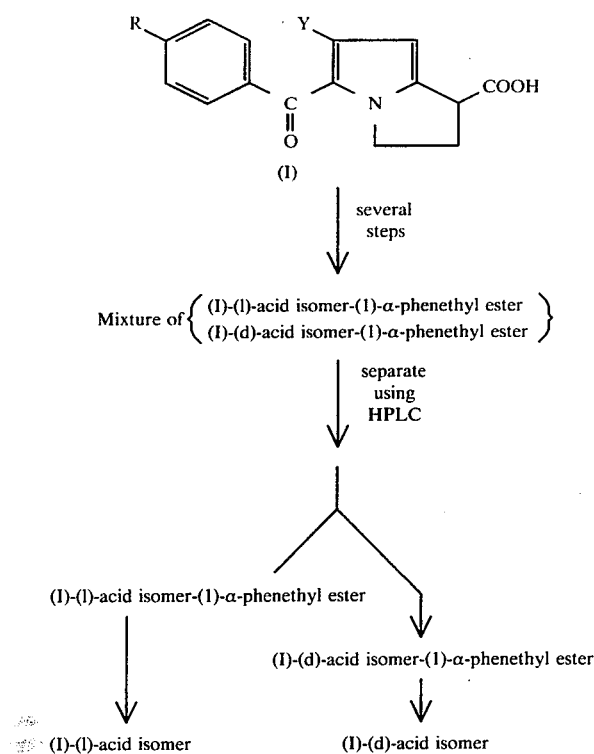

A more detailed description of this procedure is set forth in Example 3 below.

The free acids of Formula (I) can be converted into other alkyl esters having from 1 to 12 carbon atoms by conventional methods e.g., by treatment with (a) the alcohol corresponding to the desired ester in the presence of a strong mineral acid, (b) an etheral diazoalkane or (c) the desired alkyl iodide in the presence of lithium carbonate. The (1)-acid isomers can be converted into their alkyl esters by the methods of (b) and (c) above.

The salt derivatives of the compounds of Formula (I) and the (1)-acid isomers thereof are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganoushydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline betaine, ethylenediamine, glucosamine, methylglucamine, theobromine, purines, piperazine, piperidine, N-ethylpiperidine, polyamine resins and the like. The reaction is conducted in water, alone or in combination with an inert, water-misible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of Formula (I) or the (1)-acid isomers thereof to base are chosen to provide the ratio desired for any particular salt. For example, for preparing the calcium salts or magnesium salts of the compounds of Formula (I) or the (1) -acid isomers thereof, the free acid starting material can be treated with at least a one-half molar equivalent of a pharmaceutically acceptable base to yield a neutral salt. When the aluminum salts of the compounds of Formula (I) or the (1)-acid isomers thereof are prepared, at least a one-third molar equivalent of the pharmaceutically acceptable base is employed if a neutral salt product is desired.

In the preferred procedure, the calcium salts and magnesium salts of the compounds of Formula (I) and (1)-acid isomers thereof can be prepared by treating the corresponding sodium or potassium salts thereof with at least a one-half molar equivalent of calcium chloride or magnesium chloride, respectively, in an aqueous solution, alone or in combination with an inert water-miscible organic solvent, at a temperature of from about 20° C. to about 100° C. Preferably, the aluminum salts of the compounds hereof can be prepared by treating the corresponding free acids with at least a one-third molar equivalent of an aluminum alkoxide, such as aluminum triethoxide, aluminum tripropoxide and the like, in a hydrocarbon solvent, such as benzene, xylene, cyclohexane and the like, at a temperature of from about 20° C. to about 115° C. Similar procedures can be used to prepare salts of inorganic bases which are not sufficiently soluble for easy reaction.

It is to be understood that isolation of the compounds described herein can be effected, if desired, by any suitable separation or purification procedure, such as, for example, extraction, filtration, evaporation, distillation, crystallization, thin-layer chromatography or column chromatography, high pressure liquid chromotography (HPLC) or a combination of these procedures. Illustrations of suitable separation and isolation procedures can be had by reference to the Examples hereinbelow. However, other equivalent separation or isolation procedures could, of course, also be used.

While the (d)-acid isomers are not used as medicinal agents per se, they can, if desired, be converted to the pharmaceutically acceptable, non-toxic esters and salts thereof according to the methods described for the conversion of the (1)-acid isomers to their pharmaceutically acceptable, non-toxic esters and salts.

UTILITY AND ADMINISTRATION

The compounds of Formula (I), the (1)-acid isomers thereof, and their pharmaceutically acceptable non-toxic esters and salts, are useful as anti-inflammatory agents, analgetic agents, platelet aggregation inhibitors, fibrinolytic agents, and as smooth muscle relaxants. These compounds can be used both prophylactically and therapeutically.

The compositions containing these compounds are thus useful in the treatment and elimination of inflammatory conditions of the muscular skeletal system, skeletal joints and tissues. For example, the pharmaceutical compositions of this invention are useful in the treatment of inflammatory conditions such as rheumatism, concussion, laceration, arthritis, bone fractures, post-traumatic conditions, and gout. In those cases in which the above conditions include pain and pyrexia, the instant compounds are useful for the relief of these conditions as well as the inflammation.

Initial small animal screening tests to determine anti-inflammatory activity potential include the carrageenin induced paw inflammation test in the rat, according to the method of Winter, et al (Proc Soc Exp. Biol Med 111:544–547, 1962) and the cotton pellet granuloma test in the rat according to the method of Meier, et al (Experientia 6:469–471,1950) and modifications thereof.

In addition, in certain cases, the anti-inflammatory activity may be evaluated by using the adjuvant arthritis assay according to the method of Pearson (Proc Soc Exp Biol Med 91:95–101, 1956). Also, in vitro tests, for example those using synovial explants from patients with rheumatoid arthritis, Dayer et al (J Exp Med 145:1399–1404, 1977), are useful in determining whether compounds exhibit anti-inflammatory activity.

Small animal screening tests to determine analgetic activity potential include the mouse analgetic (antiwrithing) assay according to the method of Hendershot and Forsaith (J Pharmacal Exp Ther 125:237–240, 1959).

Generally, the antipyretic activity potential is indicated by the anti-inflammatory potential as measured by the previously mentioned assays.

Platelet aggregation inhibition potential is determined by using the turbidimetric method of Born (J Physiol (Lond) 162:67–68 p, 1962).

Potential activity as a smooth muscle relaxant is determined in vitro using the method of Vickery (Prostaglandins Med, 2:299–315, 1979) or Vickery (Prostaglandins Med, 2:225–235, 1979).

Administration of the active compounds of Formula (I) or the (1)-acid isomers thereof and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof. Thus, the route of administration can be oral, parenteral or otherwise systemic, or topical. The dosage form may be solid, semi-solid, or liquid in a variety of configurations and vehicles, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of Formula (I) or the (1) isomer thereof and the pharmaceutically acceptable, non-toxic esters and salts thereof, and, in addition, may include other medicinal agents, pharmaceutical agents, carriers, adjuvants, etc.

The preferred manner of administration for treatment of the conditions detailed above is oral, using a convenient daily dosage regimen which can be adjusted according to the degree of affliction. Generally, a daily dose of from 0.02 to 20 mg/kg of body weight per day of the active compound of Formula (I) and the pharmaceutically acceptable, non-toxic esters and salts thereof is used. Most conditions respond to a treatment comprising a dosage level of the order of 0.05 to 2 mg. per kilogram of body weight per day. Thus, for administration to a 70 kg person, the dosage range per day would be about 1.4 to 1400 mg per day, preferably about 3.5 to 140 mg per day.

For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like, a disintegrant such as starch or derivatives thereof, a lubricant such as magnesium stearate or the like, and a binder such as a starch, gum acacia, polyvinylpyrrolidone, gelatin, cellulose and derivatives thereof, or the like.

Generally, the pharmaceutically acceptable compositions will contain about 1% to about 90% by weight of the pharmaceutically active compound of this invention and 99% to 10% by weight of suitable pharmaceutical excipients. Preferably, the composition will be about 3.5 to 60% by weight of a pharmaceutically active compound, with the rest being suitable pharmaceutical excipients.

The active compounds of Formulas (I) and the pharmaceutically acceptable, non-toxic esters and salts thereof, may be formulated into a suppository using, for example, polyethylene glycols (PEG), for example, PEG 1000 (96%) and PEG 4000 (4%), as the carrier. Liquid pharmaceutically administerable compositions can be prepared by, for example, dissolving, dispersing, etc. an active compound, as described above, and optional pharmaceutical adjuvants, in a carrier such as water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pa., 14th. Edition, 1970. The composition to be administered will, in every case, contain a therapeutically effective quantity of the active compound(s) for relief of the particular condition being treated, in accordance with the teachings of this invention.

The compounds of Formula (I) and the non-toxic, pharmaceutically acceptable, esters and salts thereof, are also uterine smooth muscle relaxants and thus are useful as agents for maintaining the pregnancy of pregnant mammals. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formula (I) and the pharmaceutically acceptable, non-toxic esters and salts thereof, are used as agents for delaying the onset of, or for postponing, parturition. As used in this application, the phrase "to delay the onset of parturition" is intended to cover that delay in parturition caused by the administration of the compounds of Formula (I) and the pharmaceutically acceptable, non-toxic esters and salts thereof, before and after uterine muscle contractions have begun. Thus, it is intended that the aforementioned phrase cover abortion prevention early in pregnancy (i.e., before the fetus is "viable") as well as delaying premature parturition, a term which sometimes is used with reference to premature labor experienced later in the pregnancy when the fetus is considered to be "viable". In either case, the agents are administered as prophylactic agents to prevent or postpone the onset of parturition. The compounds of Formula (I) are particularly useful in the treatment of women having a history of spontaneous abortion, miscarriage or premature delivery (i.e., delivery prior to full term). They are also useful where there are clinical indications that the pregnancy might be terminated prior to full term and such premature termination is considered undesirable.

When the compounds of Formula (I) are used to delay parturition after uterine contractions have begun, the condition of the patient, including the time within the gestation period when the contractions have begun, the severity of the contractions, and how long the contractions have taken place, will affect the results achieved with the administration of the compounds hereof. For example, the effect can be to reduce the intensity and/or the duration of the contractions (the actual act of parturition being "prolonged"), or to stop the contractions altogether. In either case, the effect will be to prolong the gestation period. However, the effect may either by slight or, under appropriate circumstances, somewhat greater depending on the parameters discussed above. Such administration may be useful to prevent spontaneous abortion, to cause the delivery to be more easily accomplished and/or less painful to the mother, or to occur at a more appropriate time and/or place.

With respect to animals, this treatment can also be utilized to synchronize the deliveries of a group of pregnant animals to occur at or about the same time, or at or about a desired time and/or place, so that the births can be handled with greater facility.

In all cases, administration of the compounds of Formula (I) and the pharmaceutically acceptable, nontoxic esters and salts thereof, as uterine smooth muscle relaxants as set forth herein should be consistent with the best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formula (I) and the pharmaceutically acceptable, non-toxic esters and salts thereof, or a pharmaceutical composition containing same, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin, sucrose, magnesium carbonate, and the like. The active compound as defined above may be formulated as suppositories using, for example, polyalkylene glycols such as polypropylene glycol, as the carrier. Liquid pharmaceutically administerable compositions can be prepared by, for example, dissolving, dispersing, or otherwise combining an active compound as defined above, and optional pharmaceutical adjuvants, in a carrier such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known or will be apparent to those skilled in this art; for example, see Remington's Pharmaceutical Sciences, Mack Publishing Company, Easton, Pa., 14th Edition, 1970. The composition or formulation to be administered will, in any event, contain a quantity of the active compound(s) in an amount effective to delay the onset of parturition or to postpone parturition if uterine contractions have already begun. Generally a daily dose of from 0.5 mg. to about 25 mg. of the active compound per kilogram of body weight will be administered, with administration being a single daily dose or up to three or four smaller dosages regularly given throughout the day. The amount of active compound administered will, of course, depend on its relative activity.

In summary, those skilled in the art may make the invention described herein by:

a process for producing a compound of the formula

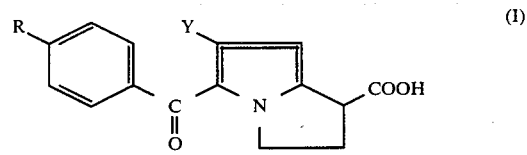

and the pharmaceutically acceptable, non-toxic alkyl esters having from 1 to 12 carbon atoms and the pharmaceutically acceptable salts thereof wherein R is vinyl or ethynyl, and Y is hydrogen, a lower alkyl having from 1 to 4 carbon atoms, chloro or bromo which process comprises:

(a) condensing a compound of the formula

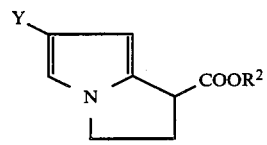

wherein Y is as defined above and $R^2$ is a lower alkyl group of 1 to 6 carbon atoms, with a compound of the formula

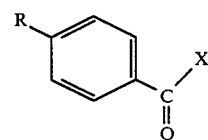

wherein R is as defined above and X is Cl, Br or NR³R⁴, wherein R³ and R⁴ are independently lower alkyl, cycloalkoxy, or morpholino, thereby yielding the corresponding compound of the formula

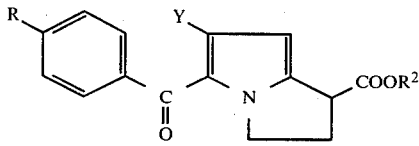

wherein R, R² and Y are as defined above; or (b) optionally hydrolyzing an alkyl ester group thereby yielding the free acid thereof; or (c) optionally esterifying the carboxylic acid function; or (d) optimally converting the carboxylic acid into pharmaceutically acceptable, non-toxic salt; or (e) optionally converting a salt to the corresponding free acid; or (f) optionally converting a salt to a corresponding pharmaceutically acceptable salt.

The following Preparations and Examples illustrate the invention but are not intended to limit its scope. The abbreviation t.l.c. refers to thin-layer chromatography and all mixture ratios used with regard to liquids refer to volume ratios. Also where necessary, examples are repeated to prepare additional material for subsequent examples; and unless otherwise specified the reactions are carried out at room temperature (20° C. to 30° C.).

In the following Preparations and Examples, the parenthetical references are to the Formulas of Reaction Sequences 1 or 2 or Formulas A, B, or C, as appropriate. The Preparations and Examples are given as representative of the compounds of this invention but are not intended to limit the scope of the invention thereto.

PREPARATION 1

Compounds of Formula B: Methyl 1,2-dihydro-3H-pyrrolo[1,2-a]pyrrole-1-carboxylate and related compounds of Formula B wherein Y=H (Roman numerals used in this Preparation refer to compounds depicted hereinabove in Reaction Sequence II.)

A. A 250 ml. 3-necked round bottomed flask containing a magnetic stirring bar and fitted with a calcium chloride filled drying tube is connected directly (via one of the outer necks) by means of a receiver adapter and short (3") water condenser to the acetal pyrolysis apparatus. This latter apparatus consists of a 100 ml. round bottomed flask [previously charged with 15.6 g. of oxalic acid dihydrate and 11.82 g. of bromoacetaldehyde diethyl acetal, prepared from vinyl acetate, as described by P. Z. Bedoukian, J. Am. Chem. Soc. 66, 651 (1944)], topped with a 6" Vigreux column, bearing a thermometer, connected to the above mentioned condenser.

The 3-necked flask is charged with 3.36 g. of ethanolamine cooled in an ice bath at 0°–10° C. and treated dropwise, with stirring, with 8.7 g. of dimethyl 1,3-acetonedicarboxylate. Methyl 3-carbomethoxymethyl-3(2'-hydroxyethyl)amino acrylate (III) forms immediately. When the addition is completed, the ice bath is removed and 100 ml. of dry acetonitrile is added. The pyrolysis part of the apparatus is placed in an oil bath and the temperature thereof is raised to 150°–160° C.

The bromoacetaldehyde solution which forms is distilled (b.p. 80°–83° C./580 mm) directly into the magnetically stirred solution of the vinylamine (III). When the distillation temperature drops below 80° C., the pyrolysis apparatus is disconnected and replaced by a reflux condenser fitted with a drying tube containing calcium chloride. The solution is heated at reflux temperature for 1 hour, the solvent is removed under reduced pressure and then 200 ml. of methanol and 20 g. of silica gel are added to the residue. This mixture is evaporated to dryness in vacuum and placed on top of a column of 200 g. of silica gel packed in hexane. The column is then eluted with hexane:ethyl acetate (80:20; 500 ml.) and hexane:ethyl acetate (1:1; 9×500 ml.). Fractions 2 and 3 contain less polar impurities and dimethyl 1,3-acetonedicarboxylate; fractions 4–8 afford 4.1 g. of methyl N-(2-hydroxyethyl)-3-carbomethoxypyrrole-2-acetate (IV, Y=H), which upon recrystallization from ether-hexane has a melting point of 52°–54° C.

B. To a stirred solution of 4.1 g. of methyl N-(2-hydroxyethyl)-3-carbomethoxypyrrole-2-acetate in 35 ml. of dry dichloromethane cooled to −10° C., are added 2.65 ml. of triethylamine and thereafter, in a dropwise fashion, 1.46 ml. of methanesulfonyl chloride, maintaining the temperature of the reaction mixture at −10° to −5° C. The course of the reaction is followed by t.l.c. analysis using chloroform:acetone (90:10). When the reaction appears to be complete (about 30 minutes after the addition of the methanesulfonyl chloride is terminated) there is added slowly 10 ml. of water. The organic phase is separated, washed with water (3×30 ml.), dried over sodium sulfate and evaporated under reduced pressure. Crystallization of the residue from dichloromethanehexane affords 4.75 g. (77.7%) of methyl N-(2-mesyloxyethyl)-3-carbomethoxypyrrole-2-acetate (V,Y=H), m.p. 99°–101° C.

C. A solution of 785 mg. of methyl N-(2-mesyl-oxyethyl)-3-carbomethoxypyrrole-2-acetate and 1.83 g. of sodium iodide in 10 ml. of acetonitrile is refluxed for 1 hour. The cooled reaction mixture is evaporated to dryness under reduced pressure and the residue is triturated with water. The insoluble material is separated by filtration and air dried, thus obtaining 840 mg. (97%) of methyl N-(2-iodo-ethyl)-3-carbomethoxypyrrole-2-acetate (VI, Y=H), m.p. 137°–138° C.

D. A solution of 1 g. of methyl N-(2-iodoethyl)-3-carbomethoxypyrrole-2-acetate in 5 ml. of dry dimethylformamide is stirred, under an atmosphere of argon, with 137 mg. of 50% sodium hydride in mineral oil. The reaction mixture is maintained for 30 minutes at room temperature and then quenched with 100 ml. of water. The product is extracted with ethyl acetate (3×50 ml.), the combined extracts are washed with water, dried over magnesium sulfate and evaporated to dryness. Chromatography of the residue on 20 g. of silica gel, using hexane:ethyl acetate (4:1) as eluant, affords 500 mg. (80%) of dimethyl 1,2-dihydro-3H-pyrrolo[1,2-a]pyrrole-1,7-dicarboxylate (VII, Y=H) m.p. 70°–71° C.

A solution of 1.80 g. of dimethyl 1,2-dihydro-3H-pyrrolo[1,2-a]pyrrole-1,7-dicarboxylate in 20 ml. of methanol is treated with a solution of 4.48 g. of potassium hydroxide in 20 ml. of water, and the reaction mixture is refluxed for 6 hours. The cooled solution is evaporated to dryness and the residue is treated with 50 ml. of saturated sodium chloride solution. The resultant solution is acidified with 6N hydrochloric acid and extracted with ethyl acetate (3×50 ml.). The combined extracts are dried over magnesium sulfate and evaporated to dryness under reduced pressure, to yield 1.51 g. (95%) of 1,2-dihydro-3H-pyrrolo[1,2-a]pyrrole-1,7-dicarboxylic acid (VIII, Y=H), m.p. 220° C., with decomposition.

E. (i) A solution of 1.34 g. of 1,2-dihydro-3H-pyrrolo[1,2-a]pyrrole-1,7-dicarboxylic acid in 50 ml. of methanol, cooled in an ice bath is saturated with gaseous hydrogen chloride, maintaining the temperature of the reaction mixture below 50° C. The ice bath is then removed and the reaction mixture is stirred for 1.5 hours at room temperature, and evaporated to dryness under reduced pressure; 10 ml. of benzene is added to the residue and the solution is evaporated under vacuum once again, repeating this process a total of three times to completely remove the excess hydrogen chloride, thus obtaining 1.58 g. (96%) of methyl 1,2-dihydro-3H-pyrrolo[1,2-a]pyrrole-1-carboxylate-7-carboxylic acid (IX, Y=H, $R^2$=CH$_3$), which upon crystallization from methanol-ethyl acetate has a melting point of 144°–145° C.

(ii) In a similar manner but substituting isopropanol, ethanol, propanol and n-butanol for methanol in the above procedure there are respectively obtained:
isopropyl 1,2-dihydro-3H-pyrrolo[1,2-a]pyrrole-1-carboxylate-7-carboxylic acid;
ethyl 1,2-dihydro-3H-pyrrolo[1,2-a]pyrrole-1-carboxylate-7-carboxylic acid;
propyl 1,2-dihydro-3H-pyrrolo[1,2-a]pyrrole-1-carboxylate-7-carboxylic acid; and
butyl 1,2-dihydro-3H-pyrrolo[1,2-a]pyrrole-1-carboxylate-7-carboxylic acid.

F. (i) 1.054 G. of isopropyl 1,2-dihydro-3H-pyrrolo[1,2-a]pyrrole-1-carboxylate-7-carboxylic acid is heated to 240°–250° C. in a dry 10 ml. round bottomed flask, distilling directly the reaction product from the reaction vessel. In this manner there is obtained 745 mg. (87%) of isopropyl-1,2-dihydro-3H-pyrrolo-[1,2-a]pyrrole-1-carboxylate (the compound of Formula B wherein Y=H, $R^2$=CH$_3$), a pale yellow oil, having the following physical constants:

U.V.: λmax MeOH 215 nm (ε 6020); I.R.: νmax CHCl$_3$ 
1725 cm$^{-1}$; N.M.R.: δTMS$^{CDCl_3}$ 1.22 (d, J=7 Hz, 6H), 2.40–2.90 (m, 2H), 3.60–4.20 (m, 2H), 4.65–5.2 (m, 1H), 5.73–5.92 (m, 1H), 6.10 (t, J=3 Hz, 1H), 6.43–6.53 ppm. (m, 1H).

(ii) In a similar manner, other alkyl acids obtained by the methods described in paragraphs A through E (ii) above can be converted to their corresponding ester derivatives of Formula B.

PREPARATION 2

Alternative preparation of methyl 1,3-dihydro-3H-pyrrolo[1,2-a]pyrrole-1-carboxylate, and related compounds of Formula B wherein Y=H A 100 ml. 3-necked round bottomed flask equipped with a condenser, nitrogen inlet tube and a gas bubbler is charged with 5.0 g. of methyl 1,2-dihydro-3H-pyrrolo-1,2-a]pyrrole-1-carboxylate-7-carboxylic acid. The apparatus is thoroughly flushed with nitrogen and then the nitrogen flow is stopped. The apparatus is immersed in an oil bath heated at 270° C. and the reaction is followed by the rate of carbon dioxide evolution (gas bubbler) and by t.l.c. on silica gel, using benzene:dioxane:acetic acid (90:10:1) as developing solvent. After 45 minutes the reaction is almost complete. After one hour, the vessel is removed from the oil bath and the contents of the reaction flask are transferred to a round bottomed flask with 500 ml. of acetone. The solvent is removed under reduced pressure, and the residue is purified by column chromatography on 100 g. of silica gel. The fractions eluted with hexane:benzene (70:30) and hexane:benzene (50:50) afford 2.77 g. (68%) of methyl 1,2-dihydro-3H-pyrrolo-[1,2-a]pyrrole-1-carboxylate (X, Y=H, $R^2$=CH$_3$), an oil, whose physical constants are identical to those obtained in Preparation 1. In a similar manner, other alkyl acids obtained by the methods described in paragraphs A through E (ii) of Preparation 1 can be converted into their corresponding ester derivatives, the compounds of Formula B.

PREPARATION 3

Preparation of isopropyl 1,2-dihydro-6-methyl-3H-pyrrolo[1,2-a]-pyrrole-1-carboxylate and related compounds of Formula B wherein Y=alkyl A. A 250 ml. 3-necked round bottomed flask containing a magnetic stirring bar and fitted with a calcium chloride filled drying tube, is charged with 3.36 g. of ethanolamine, cooled in an ice bath at 0°–10° C. and treated dropwise, with stirring, with 8.7 g. of dimethyl 1,3-acetonedicarboxylate. Methyl 3-carbomethoxymethyl-3-(2'-hydroxyethyl)amino acrylate (III) forms immediately. When the addition is completed, the ice bath is removed and 80 ml. of dry acetonitrile is added. The reaction mixture is then treated dropwise with 6.75 g. of bromoacetaldehyde in 20 ml. of acetonitrile and thereafter heated at reflux temperature for 2 hours. The solvent is then removed under reduced pressure and 200 ml. of methanol and 20 g. of silica gel are added to the residue. This mixture is evaporated to dryness in vacuum and placed on top of a column of 200 g. of silica gel packed in hexane, eluting the column with hexane:ethyl acetate mixtures. The fractions eluted with hexane:ethyl acetate (1:1) afford methyl N-(2-hydroxyethyl)-3-carbomethoxy-pyrrole-2-acetate (IV, Y=H) identical to the product obtained in Preparation 1.A.

B. To a solution of 6 ml. of ethanolamine in 5 ml. of water there is added 1.74 g. of dimethyl 1,3-acetonedicarboxylate. The resultant mixture is rapidly cooled to −10° C. and treated dropwise, over a 15 minute period, with stirring, with 1.67 ml. of 1-bromoacetone, while maintaining the reaction mixture at a temperature not higher than 40° C. When the addition is completed the reaction mixture is stirred for an additional hour at room temperature, and then poured into a mixture of hydrochloric acid-ice, saturated with solid sodium chloride and extracted with ethyl acetate (3×100 ml.). The combined organic extract is washed with cold water to neutrality, dried with anhydrous sodium sulfate and evaporated to dryness under reduced pressure. Chromatography of the residue on 30 g. of silica gel, using hexane:ethyl acetate (70:30) as eluant, carbomethoxy-4-methylpyrrole-2-acetate, which, upon recrystallization from methylene chloride-hexane, melts at 78° C. and has the following analysis:
Calculated for $C_{13}H_{17}NO_5$: C, 56.45; H, 6.71; Found: C, 56.41; H, 6.73.

In a similar manner but using a stoichiometric equivalent of 1-bromo-2-butanone, 1-bromo-2-pentanone, and 1-bromo-2-hexanone in the place of 1-bromoacetone there are respectively obtained:

methyl N-(2-hydroxyethyl)-3-carbomethoxy-4-ethyl-pyrrole-2-acetate, m.p. 64°-65° C.;

methyl N-(2-hydroxyethyl)-3-carbomethoxy-4-propyl-pyrrole-2-acetate; and methyl N-(2-hydroxyethyl)-3-carbomethoxy-4-butyl-pyrrole-2-acetate.

C. By following the methods of Preparation I, paragraphs B, C, D and E methyl N-(2-hydroxyethyl)-3-carbomethoxy-4-methylpyrrole-2-acetate (IV, Y=CH$_3$) is converted successively into:

methyl N-(2-mesyloxyethyl)-3-carbomethoxy-4-methylpyrrole-2-acetate;

methyl N-(2-iodoethyl)-3-carbomethoxy-4-methylpyrrole-2-acetate;

dimethyl 1,2-dihydro-6-methyl-3H-pyrrolo[1,2-a]-pyrrole-1,7-dicarboxylate;

1,2-dihydro-6-methyl-3H-pyrrolo[1,2-a]-pyrrole-1,7-dicarboxylic acid;

isopropyl 1,2-dihydro-6-methyl-3H-pyrrolo[1,2-a]-pyrrole-1-carboxylate-7-carboxylic acid; and isopropyl 1,2-dihydro-6-methyl-3H-pyrrolo[1,2-a]-pyrrole-1-carboxylate (B, Y=CH$_3$, R$^2$=iC$_3$H$_7$).

In a similar manner substituting methyl N-(2-hydroxyethyl)-3-carbomethoxy-4-ethylpryrrole-2-acetate, methyl N-(2-hydroxyethyl)-3-carbomethoxy-4-propyl-pyrrole-2-acetate and methyl N-(2-hydroxyethyl)-3-carbomethoxy-4-butylpyrrole-2-acetate for methyl N-(2-hydroxyethyl)-3-carbomethoxy-4-methylpyrrole-2-acetate there are respectively obtained as final products the following compounds of Formula B wherein Y is alkyl:

isopropyl 1,2-dihydro-6-ethyl-3H-pyrrolo[1,2-a]-pyrrole-1-carboxylate;

isopropyl 1,2-dihydro-6-propyl-3H-pyrrolo[1,2-a]-pyrrole-1-carboxylate; and isopropyl 1,2-dihydro-6-butyl-3H-pyrrolo[1,2-a]-pyrrole-1-carboxylate.

Other corresponding methyl, ethyl and butyl esters are similarly prepared.

PREPARATION 4

Preparation of the compound of Formula B wherein Y is chloro or bromo:

Methyl 6-chloro-1,2-dihydro-3H-pyrrolo[1,2-a]pyrrole-1-carboxylate and

Methyl 6-bromo-1,2-dihydro-3H-pyrrolo[1,2-a]pyrrole-1-carboxylate (Formula identifications refer to compounds depicted hereinabove in Reaction Sequence III.)

A. Ethyl 1-(2-acetoxyethyl)pyrrole-2-glyoxalate (Formula 4)

Acetic acid (32.2 l) is charged to a reactor, and 26.1 kg of ethanolamine is charged over a 1 hour period, keeping the temperature below 54°, thereto. The resulting mixture is cooled to 28° C., 2,5-dimethoxytetrahydrofuran (12.5) is charged to the reactor, and the contents are heated at 115°–119° for 8 hours, then cooled to 20°. The mixture is diluted with saturated sodium chloride solution (80 l) and water (54 l) and extracted with two 80 l volumes of ethylacetate. The extracts are washed with 80 l saturated sodium chloride solution, 80 l saturated sodium bicarbonate solution and twice with 80 l saturated sodium chloride solution. The organic layers are dried with 5 lbs sodium sulfate and evaporated in vacuo to 40 l. This solution is treated with 13.5 kg silica gel and 40 l hexane for 15 minutes. The silica gel is removed by filtration and washed with 80 l 1:1 ethylacetate/hexane, then with 5 l of the same solvent mixture. The filtrate and washings are evaporated to near dryness in vacuo. The residue is dissolved in 10 l methanol and evaporated to dryness. This methanol evaporation is then repeated. The residue is dissolved in 40 l methanol and 39.65 g of sodium is added to the solution. This solution is heated at reflux temperature for 45 minutes and then cooled to 20° C. Acetic acid (98.5 ml) is added to the solution. The resulting solution is evaporated to dryness to afford 1-(2-hydroxyethyl)-pyrrole (Formula 2).

The resulting product is reacted with acetic anhydride in accordance with the method of F. F. Blicke and E. S. Blake, *J. Am. Chem. Soc.*, 53, 1015(1931). A mixture of 1-(2-hydroxyethyl)pyrrole (147 g, 1.32 mole), pyridine (415 ml) and acetic anhydride (139 ml) is heated on a steam bath for 0.5 hours. The reaction mixture is cooled to room temperature, poured into water (one l) and the product is extracted into ethyl acetate (3×1 l). The extract is washed successively with dilute hydrochloric acid, saturated sodium chloride solution, dilute sodium bicarbonate solution, and again with saturated sodium chloride solution. The extract is dried over sodium sulfate, evaporated in vacuo and the residue (150 g) is subjected to column chromatography on Florisil ® activated magnesium silicate. The desired product is eluted with hexane-dichloromethane (1:1) to give 128 g (55%) 1-(2-acetoxyethyl)pyrrole, an oil.

A solution of pyridine (89 ml) in anhydrous dichloromethane (2 l) is added to a stirred and cooled solution of ethoxalyl chloride (136 g, 1 mole) in dry dichloromethane (2 l) at a rate such that the reaction temperature is maintained at −20° to −25° C. Upon completion of this addition, a solution of 1-(2-acetoxyethyl)pyrrole (128 g, 0.84 mole) in dry dichloromethane (2 l) is added at a rate such that the reaction temperature is maintained at −20° to −0° C. The reaction mixture is then stirred at −20° to 0° C. for 2 hours and at ambient temperature for 16 hours. The reaction mixture is then washed successively with dilute hydrochloric acid, dilute sodium bicarbonate solution and water. The organic phase is dried over sodium sulfate and evaporated in vacuo to give 211 g of an oily residue which is subjected to column chromatography on Florisil ® activated magnesium silicate. The product is eluted with hexane-ethyl acetate (first 19:1 then 4:1) to give (151 g, 71%) ethyl 1-(2-acetoxyethyl)pyrrole-2-glyoxalate (Formula 4) as an oil having the following physical characteristics:

U.V. 208 sh, 245, 311 nm (ε 2820, 4170, 11,800)
I.R. (CHCl$_3$) 1740, 1665 cm$^{-1}$
M.S. 253 (M+)

B. Ethyl 1-(2-acetoxyethyl)-4-chloropyrrole-2-glyoxalate (Formula 5) where Y is Cl The resulting ethyl 1-(2-acetoxyethyl)pyrrole-2-glyoxalate prepared as in Preparation 4A (40.5 g, 0.16 mol.) is dissolved in anhydrous dichloromethane (900 ml) and cooled to −70°. Recently distilled sulfuryl chloride (13.7 ml, 0.17 mole) is added in a dropwise manner. When the addition is completed, the solution is allowed to come to room temperature spontaneously. After two hours at this temperature TLC (silica gel;

hexane:ethyl acetate; 80:20) shows the absence of starting material. The solvent is removed in vacuo and the oily residue is dissolved in dichloro-methane (300 ml) and washed to neutrality with water. The organic phase is dried over sodium sulfate and evaporated to dryness in vacuo. The residue, which weighed 63 g. is purified by column chromatography on silica gel (800 g) using hexane ethyl acetate (90:10) as the eluting solvent. This procedure yields 19 g (41% yield) of ethyl 1-(2-acetoxyethyl)4-chloropyrrole-2-glyoxalate (Formula 5 where Y is Cl) having the following physical constants:

U.V. 275, 310 nm ($\epsilon$ 5630, 9340)
I.R. 1743, 1654 cm$^{-1}$ (CHCl$_3$)
N.M.R. (CDCl$_3$)
1.44 (t, 3H, J=7.2)
2.07 (s, 3H)
4.00 (s, 2H)
4.23-4.70 (m, 6H)
7.00 (d, J=1.8, 1H)
7.27 (d, J=1.8, 1H)
M.S. 287 (M+)
Calcd. for $C_{12}H_{15}ClNO_5$: C, 50.09; H, 4.90; Cl, 12.32.
Found: C, 50.12; H, 4.95; Cl, 12.35.

C. Ethyl 1-(2-acetoxyethyl)-4-bromopyrrole-2-glyoxalate (Formula 5) where Y is Br Three ml. (58.3 mmole) of bromine is added in a dropwise manner to a stirred solution of 14.77 g. (58.3 mmole) of ethyl 1-(2-acetoxyethyl)pyrrole- 2-glyoxalate in 200 ml. anhydrous dichloromethane and cooled to −75° C. After the addition, the reaction is left at −75° C. for 2.5 hours and then the temperature is allowed to increase to room tempearture. The solvent is removed in vacuo, dichloromethane is added to the residue and the solution is washed successively with water, 10% sodium bicarbonate solution and water. The organic phase is dried over sodium sulfate, and the solvent is removed in vacuo. The crude product thus obtained (18.3 g) is subjected to column chromatography on Florisil (1 Kg) using hexane-ethyl acetate (9:1) as the eluting solvent. There is thus obtained upon removal of the solvent, 10.9 g (56%) of ethyl 1-(2-acetoxyethyl)-4-bromopyrrole-2-glyoxalate as an oil having the following physical constants:

U.V. 270,310 nm ($\epsilon$ 5500, 8910)
I.R. (CHCl$_3$) 1736, 1650 cm$^{-1}$
N.M.R. (CDCl$_3$)
1.41 (t, 3H, J=7.4)
2.03 (s, 3H)
4.20-4.70 (m, 6H)
7.00 (d, 1H, J=1.8)
7.33 (d, 1H, J=1.8)
M.S. 331, 333 (M+)
Calcd. for $C_{12}H_{14}BrNO_5$: C, 43.38; H, 4.24; Br, 24.06.
Found: C, 43.33; H, 5.29; Br, 24.01.

D. Ethyl 1-(2-acetoxyethyl)-4-chloropyrrol-2-acetate (Formula 7 where Y is Cl)

A solution of water (25 ml) in methanol (300 ml) is cooled in a dry ice:carbon tetrachloride:acetone bath to −30° and 23.7 g of sodium borohydride is added thereto. When the violent reaction has subsided, there is added, in a dropwise manner, 40 g. (0.139 moles) of ethyl 1-(2-acetoxyethyl)-4-chloropyrrole-2-glyoxalate dissolved in methanol (400 ml.) at a rate such that the temperature does not exceed −20° C. The reaction is maintained at this temperature for two hours when there is added a solution of 21.5 ml. of acetic acid in 320 ml water. The solution is stirred for a further 1 hour at −30° during which time a white precipitate forms. This solid is collected by filtration and dissolved in dichloromethane. The organic solution was washed with saturated sodium chloride solution, dried over sodium sulphate and evaporated in vacuo. There is obtained 33.15 g. of a solid product which is homogeneous by thin layer chromatography. Recrystallization from dichloromethane-hexane yields ethyl 1-(2-acetoxyethyl)-4-chloropyrrole-2-glycolate, m.p. 60°-61° C. (Formula 6 where Y is Cl).

In an argon atmosphere, 27.9 g (0.11 moles) of iodine is dissolved in 400 ml. of dry benzene and 57.7 g (0.22 moles) of triphenylphosphine is added. After stirring for 5-10 minutes 32.0 g (0.11 moles) of the 1-hydroxyacetate is added all at once. The mixture is heated at reflux temperature for 2.5 hours. During this time triphenylphosphine oxide separated from solution. At the end of the reaction the mixture is cooled and the solids are separated by filtration. The filtrate is washed with 10% aqueous sodium bicarbonate solution and then with a saturated solution of sodium chloride in water. The solution is dried over sodium sulphate and evaporated to dryness in vacuo. The resulting dark colored oil is purified by column chromatography on Florisil ® brand activated magnesium silicate using hexane-ethyl acetate (90:10) as the eluting solvent to give 26 g (83% yield) of ethyl 1-(2-acetoxyethyl)-4-chloropyrrol-2-acetate (Formula 7 where Y is Cl) having the following physical constants:

U.V. 218 nm ($\epsilon$ 6460)
I.R. 1736 cm$^{-1}$ (CHCl$_3$)
N.M.R. (CDCl$_3$)
1.24 (t, 3H, J=7.1)
2.05 (s, 3H)
3.60 (s, 2H)
3.93-4.40 (m, H)
6.00 (d, 1H, J=1.8)
6.60 (d, 1H, J=1.8)
M.S. 273 (M+)
Calcd. for $C_{12}H_{16}ClNO_4$: C, 52.65; H, 5.89; N, 5.11.
Found: C, 52.57; H, 5.90; N, 5.09.

E. Ethyl 1-(2-acetoxyethyl)-4-bromopyrrol-2-acetate (Formula 7 where Y is Br)

Methanol (100 ml) containing 2.5 ml water is cooled to −50° C. and 3.07 g of sodium borohydride (81.2 mmole) is added with stirring. After 5 minutes, ethyl 1-(2-acetoxyethyl)-4-bromopyrrole-2-glyoxalate (8.9 g −26.7 mmole) is dissolved in 40 ml methanol and added at a rate such that the reaction temperature does not exceed −40° C. After 1 hour at this temperature, 50% aqueous acetic acid is added until the solution is weakly acidic. The methanol is then removed in vacuo, 100 ml ethyl acetate is added to the residue, and the organic phase is washed well with saturated salt solution and then dried over sodium sulfate. The solvent is removed in vacuo and the residue is immediately crystallized, at low temperature (dry ice-acetone bath), from ether. The ethyl 1-(2-acetoxyethyl)-4-bromopyrrole-2-glycolate thus obtained (6.0 g, 67%) exhibits a m.p. of 59° C. but is unstable and is be stored in an evacuated vessel at −10° C.

Triphenylphosphine (15.2 g, 58.0 mmole) is added to a solution of iodine (7.37 g, 29.0 mmole) in anhydrous benzene (300 ml) maintained in a nitrogen atmosphere. After agitation for 10 minutes, a solution of the ethyl glyoxalate (9.7 g, 29.0 mmole) in dry benzene (100 ml) is added all at once. The resultant is left at room temperature for 18 hours. The solid which precipitates is collected by filtration, washed well with ether, and the filtrate evaporated in vacuo. The residue is dissolved in dichloromethane, washed well with saturated salt solution, dried and evaporated. The material thus obtained is subjected to column chromatography on silica gel (400 g) using hexane-ethyl acetate (9:1 and then 4:1) to elute the product. A few drops of triethylamine is added to each fraction collected from the column stablize the product. Upon removal of the solvent, there is obtained 7.9 g, (86%) of ethyl 1-(2-acetoxyethyl)-4-bromopyrrol-2-acetate, an unstable oil exhibiting the following characteristics:

U.V. 218, 307 nm ($\epsilon$ 6610, 275)
I.R. ($CHCl_3$)
N.M.R. ($CDCl_3$)
  1.25 (t, 3H, J=7.3)
  2.05 (s, 3H)
  3.60 (s, 2H)
  3.98–4.34 (m, 6H)
  6.07 (d, 1H, J=1.8)
  6.66 (d, 1H, J=1.8)

F. Alkyl 1-(2-Hydroxyethyl)4-chloropyrrol-2-acetate (Formula 8 where Y is Cl)

Twenty-six g of ethyl 1-(2-acetoxyethyl)-4-chloropyrrole-2-acetate (0.095 ml) is dissolved in 260 ml. of anhydrous methanol and 10 drops of DBN is added. The solution is stirred at room temperature, in a nitrogen atmosphere, for 6 hours. Two and a half l of an aqueous saturated solution of sodium chloride is added and the product is extracted into ethyl acetate. The organic phase is washed with a saturated sodium chloride solution, dried over sodium sulphate and evaporated in vacuo to give 20.1 g. of methyl 1-(2-hydroxyethyl)-4-chloropyrrol-2-acetate (Formula 8, Y is Cl), an oil having the following physical constants:

U.V. 207.5, 216 nm ($\epsilon$ 6030, 5090)
I.R. 3590, 3500, 1732 cm$^{-1}$ ($CHCl_3$)
N.M.R ($CDCl_3$)
  2.74 (s, $W_H$=4, exchanged with $D_2O$)
  3.58 (s, 2H)
  3.61–3.92 (m, 4H)
  3.67 (s, 3H)
  6.27 (d, 1H, J=2.0)
  6.58 (d, 1H, J=2.0)
M.S. 217 (M+)
Calcd. for $C_9H_{12}ClNO_3$: C, 49.66; H, 5.55; N, 6.43.
Found: C, 49.63; H, 5.46; N, 6.53.

G. Methyl 1-(2-hydroxyethyl)-4-bromopyrrol-2-acetate (Formula 8 where Y is Br)

A solution of 8.0 g (25.0 mmole) of the pyrrole from Preparation (4), Part E, in 100 ml anhydrous methanol containing 1,5-diazabicyclo[4.3.0]nonene-5 (5 drops) is left at room temperature in an argon atmosphere for 18 hours. The solvent is removed in vacuo, the residue is dissolved in ethyl acetate, the solution washed with saturated salt solution, dried over sodium sulfate and evaporated in vacuo to give methyl 1-(2-hydroxyethyl)-4-bromopyrrole-2-acetate, (8, Y is Br) an oil having the following physical constants:

U.V. 218 nm ($\epsilon$ 5620)
I.R. ($CHCl_3$) 3600, 3520, 3440, 1740 cm$^{-1}$
N.M.R. ($CDCl_3$)
  2.78 (s, 1H, exchanged with $D_2O$)
  3.55–4.02 (m, 4H)
  3.65 (s, 2H)
  3.72 (s, 3H)
  6.06 (d, 1H, J=1.5)
  6.71 (d, 1H, J=1.5)

H. Methyl 1-(2-iodoethyl)-4-chloropyrrol-2-acetate (Formula 10 where Y is Cl)

Twenty g. (0.092 moles) of methyl 1-(2-hydroxyethyl)-4-chloropyrrol-2-acetate is dissolved in 500 ml of anhydrous dichloromethane and cooled to 0°. Methanesulfonyl chloride (8.53 ml, 0.11 moles) is added all at once and after stirring for 5 minutes, 15.3 ml. of triethylamine (0.11 moles) is added in a dropwise manner. The reaction mixture is then stirred at room temperature for 1 hour. The solvent is removed in vacuo and the residue is dissolved in dichloromethane, washed with aqueous saturated sodium chloride until neutral, dried over sodium sulphate and evaporated in vacuo to give 29.8 g. of a crude methyl 1-(2-methanesulfonyloxyethyl)-4-chloropyrrol-2-acetate (Formula 9, Y is Cl).

Twenty-nine grams of the resulting mesylate (0.098 mol.) is dissolved in 700 ml of acetonitrile and 73 g of anhydrous sodium iodide (0.49 moles) is added. The mixture is heated at reflux temperature for 2 hours. The precipitate which forms is removed by filtration and washed with dichloromethane. The filtrate is evaporated to dryness in vacuo and the residue is dissolved in ethyl acetate, washed to neutrality with water, dried over sodium sulphate and evaporated in vacuo. The crude product (32.9 g) is purified by column chromatography on silica gel using hexane-ethyl acetate (95:5) as the developing solvent to give 26.1 g. methyl 1-(2-iodoethyl)-4-chloropyrrol-2-acetate (Formula 10, Y is Cl), an oil having the following physical constants:

U.V. 221.5 nm ($\epsilon$ 7250)
I.R. 1736 cm$^{-1}$ ($CHCl_3$)
N.M.R. ($CDCl_3$)
  3.29 (t, 2H, J=7.5)
  3.57 (s, 2H)
  3.70 (s, 3H)
  4.15 (t, 2H, J=7.5)
  5.98 (d, 2H, J=1.8)
  6.67 (d, 2H, J=1.8)
M.S. 327,329 (M+)

I. Methyl 1-(2-methanesulfonyloxyethyl)-4-bromopyrrol-2-acetate (Formula 9 where Y is Br.)

To a stirred solution of 5.8 g, (22.0 mmole) of the pyrrole of Preparation VI, Part B, in anhydrous dichloromethane (60 ml), cooled to 0° C. and maintained in an atmosphere of argon, is added 2.0 ml (26.5 mmole) of methanesulfonyl chloride followed by 3.7 ml (26.4 mmole) of triethylamine, added dropwise. The reaction is left to come to room temperature and after a further 30 minutes the solvent is removed in vacuo. The residue is dissolved in dichloromethane, washed well with saturated salt solution, dried and evaporated. The residue is subjected to column chromatography on silica gel (after the addition of a few drops of triethylamine) using hexane-ethyl acetate (7:3) to give a solution which, when evaporated, gives 6.0 g (80%) of methyl 1-(2-methanesulfonyloxyethyl)-4-bromopyrrol-2-acetate (Formula 9, Y is Br), an oil having the following physical constants:

U.V. 223 nm ($\epsilon$ 5370)
I.R. ($CHCl_3$) 1744, 1356, 1166, cm$^{-1}$

N.M.R. (CDCl$_3$)
  2.85 (s, 3H)
  3.60 (s, 2H)
  3.69 (s, 3H)
  4.02–4.48 (m, 4H)
  6.06 (d, 1H, J=1.6)
  6.68 (d, H, J=1.6)

J. Methyl 6-chloro-1,2-dihydro-3H-pyrrolo[1,2-a]pyrrole-1-carboxyate (Formula B where Y is Cl)

A. In an atmosphere of argon, 2.52 g of 50% sodium hydride in mineral oil (0.053 moles) is washed free of the carrier with dry hexane (2×20 ml.). Thereafter 150 ml of anhydrous dimethylformamide is added and the mixture is cooled to 0°. To this mixture is added, with stirring, 16.4 g. of methyl 1-(2-iodoethyl)-4-chloropyrrol-2-acetate (0.05 moles) dissolved in 50 ml dimethylformamide. The reaction mixture is left at room temperature for 2 hours, when saturated aqueous sodium chloride solution is added and the product extracted into benzene (3×200 ml). The organic extract is washed with water (2×100 ml), dried over sodium sulphate and evaporated in vacuo. The crude product (8.52 g) is purified by column chromatography on silica gel (245 g) using hexane-ethyl acetate (90:10) as the eluting solvent, to yield methyl 6-chloro-1,2-dihydro-3H-pyrrolo[1,2-a]pyrrole-1-carboxylate, an oil having the following physical constants:

U.V. 224, 279, 286 nm ($\epsilon$ 6760, 7420, 6920)
I.R. 1726 cm$^{-1}$ (CHCl$_3$)
N.M.R. (CDCl$_3$)
  2.37–2.75 (m, 2H)
  3.62 (s, 3H)
  3.53–4.07 (m, 3H)
  5.85 (m, 1H)
  6.45 (m, 1H)
M.S. 201.199 (M+)

K. Methyl 6-bromo-1,2-dihydro-3H-pyrrolo[1.2-a]pyrrole-1-carboxylate (Formula B where Y is Br)

Sodium hydride in mineral oil (50%, 0.65 g, 13.6 mmole) is washed free of the carrier with hexane, covered with anhydrous dimethylformamide (20 ml) and then cooled to 0°, in a nitrogen atmosphere, with stirring. The methanesulfonate (4.4 g, 12.9 mmole), prepared in accordance with Preparation 4.I, in 10 ml of dry dimethylformamide is added in a dropwise manner. The reaction mixture is left at 0° for 3 hours, at which time saturated salt solution (30 ml) is added. The product is extracted into benzene, the extract is washed with water, dried and evaporated. The residue is purified by TLC on silica gel using hexane-ethyl acetate (4:1) as the developing solvent. This yields 1.56 g (49%) of an oil which is crude methyl 6-bromo-1,2-dihydro-3H-pyrrolo[1,2-a]pyrrole-1-carboxylate.

Purification gave an oil with the following physical constants:

N.M.R. (CDCl$_3$)
  2.64–2.87 (m, 2H)
  3.73 (s, 3H)
  3.91–4.15 (m, 3H)
  6.02 (t, 1H, J$_{1,7}$ J$_{5,7}$ 1.2 Hz)
  6.69 (t, 1H, J$_{5,7}$=1.3 Hz)
M.S. m/e 242.9888, 244.9879 (M+)
calcd. for C$_9$H$_{10}$$^{79}$BrNO$_2$: 242.9895
calcd. for C$_9$H$_{10}$$^{21}$BrNO$_2$: 244.9874.

EXAMPLE 1

5-(4-Vinylbenzoyl)-1,2-dihydro-3H-pyrrolo[1,2-a]pyrrole-1-carboxylic acid

A. Methyl 5-(4-vinylbenzoyl)-1,2-dihydro-3H-pyrrolo[1,2-a]pyrrole-1-carboxylate A solution of methyl 1,2-dihydro-3H-pyrrolo[1,2-a]pyrrole-1-carboxylate (Formula B where Y is hydrogen) the synthesis of which is described in Preparations 1 and 2 hereinabove, (3.0 g, 18 mmol) and the acid chloride of 4-vinylbenzoic acid [J. Chem. Education, 55, 813 (1978)] (10.0 g, 60 mmol) in anhydrous xylene (100 ml) was heated at reflux temperature for 6 hours. The solvent was removed in vacuo and the residue was purified by column chromatography on Act II neutral alumina (Fluka, 200 g). The product was eluted with hexane-ethyl acetate (95:5) to give 5-(4-vinylbenzoyl)-1,2-dihydro-3H-pyrrolo[1,2,a]pyrrole-1-carboxylic acid, (36%) which had mp 99°–100° after crystallization from methanol. The purified product exhibited the following characteristics:

U.V. 211, 225 sh, 278, 321 nm ($\epsilon$ 14,800; 11,800; 12,900; 21,400)
N.M.R (CDCl$_3$)
  2.91 (m, 2H)
  3.78 (s, 3H)
  4.50 (m, 2H)
  4.66 (t, 1H)
  5.76 (m, 3H)
  6.76 (m, 2H)
  7.46 (d, 2H, J=8 Hz)
  7.80 (d, 2H, J=8 Hz)
M.S. 295 (M+)
Calcd. for C$_{18}$H$_{17}$ClNO$_3$: C, 73.20; H, 5.80; N, 4.74. Found: C, 72.96; H, 5.74; N, 4.59.

In a similar manner but substituting the lower alkyl esters whose synthesis is described in Preparations 1 and 2, above, for the methyl 1,2-dihydro-3H-pyrrolo[1,2-a]pyrrole-1-carboxylate in the above procedure, there are respectively obtained:

isopropyl 5-(4-vinylbenzoyl)-1,2-dihydro-3H-pyrrolo[1,2-a]pyrrole-1-carboxylate;
ethyl 5-(4-vinylbenzoyl)-1,2-dihydro-3H-pyrrolo[1,2-a]pyrrole-1-carboxylate;
propyl 5-(4-vinylbenzoyl)-1,2-dihydro-3H-pyrrolo[1,2-a]pyrrole-1-carboxylate; and
butyl 5-(4-vinylbenzoyl)-1,2-dihydro-3H-pyrrolo[1,2-a]pyrrole-1-carboxylate.

B. 5-(4-Vinylbenzoyl)-1,2-dihydro-3H-pyrrolo[1,2-a]-pyrrole-1-carboxylic acid A solution of sodium hydroxide (0.30 g, 7.5 mmol) in water (10 ml) was added to a stirred suspension of the above ester (1.40 g, 4.7 mmol) in methanol (10 ml) at 0°. The mixture was then agitated at room temperature for 5 hours, the methanol was removed in vacuo and the residue was extracted with ether. The aqueous phase was cooled to 5° and made acidic to pH 2 with concentrated hydrochloric acid. The product was extracted into ethyl acetate, the extract was washed with water, dried over sodiumn sulfate and evaporated in vacuo to give 5-(4-vinylbenzoyl)-1,2-dihydro-3H-pyrrolo[1,2-a]pyrrole-1-carboxylic acid. The residual solid (88% yield) had a mp of 155°–157° after crystallization from acetone-hexane and exhibited the following properties:

U.V. 211, 224, 276, 324 nm (ε 14,100; 11,000; 12,300; 20,400)
I.R. 1718, 1613 cm$^{-1}$ (CHCl$_3$)
N.M.R (CDCl$_3$)
  2.86 (m, 2H)
  4.10 (t, 1H)
  4.55 (m, 2H)
  5.75 (m, 2H)
  6.20 (d, 1H, J=4 Hz)
  6.85 (m, 1H)
  6.90 (d, 1H, J=4 Hz)
  7.53 (d, 2H, J=8 Hz)
  7.86 (d, 2H, J=8 Hz)
M.S. 281 (M+)
Calcd. for C$_{17}$H$_{15}$NO$_3$: C, 72.58; H, 5.37; N, 4.97. Found: C, 72.54; H, 5.44; N, 4.94.

In a similar manner, but substituting the esters described in paragraph A of this example for the methyl 5-(4-vinylbenzoyl)-1,2-dihydro-3H-pyrrolo[1,2-a]pyrrole-1-carboxylate in the above procedure, the identified compound of Formula I is obtained.

C. In a similar manner, but substituting the compounds of Formula B wherein Y is methyl, ethyl, propyl or butyl, for the methyl 1,2-dihydro-3H-pyrrolo[1,2-a]pyrrole-1-carboxylate in the procedures described in paragraphs A and B of this Example, the following compounds of Formula I are obtained:
5-(4-vinylbenzoyl)-1,2-dihydro-6-methyl-3H-pyrrolo[1,2-a]pyrrole-1-carboxylic acid;
5-(4-vinylbenzoyl)-1,2-dihydro-6-ethyl-3H-pyrrolo[1,2-a]pyrrole-1-carboxylic acid;
5-(4-vinylbenzoyl)-1,2-dihydro-6-propyl-3H-pyrrolo[1,2-a]pyrrole-1-carboxylic acid; and
5-(4-vinylbenzoyl)-1,2-dihydro-6-butyl-3H-pyrrolo[1,2-a]pyrrole-1-carboxylic acid.

D. In a similar manner, but substituting the compounds of Formula B wherein Y is chloro or bromo, the synthesis of which is described in Preparation 4 hereinabove, for the methyl 1,2-dihydro-3H-pyrrolo[1,2-a]pyrrole-1-carboxylate in the procedures described in paragraphs A and B of this Example, the following compounds of Formula I are obtained:
5-(4-vinylbenzoyl)-1,2-dihydro-6-chloro-3H-pyrrolo[1,2-a]pyrrole-1-carboxylic acid; and
5-(4-vinylbenzoyl)-1,2-dihydro-6-bromo-3H-pyrrolo[1,2-a]pyrrole-1-carboxylic acid.

EXAMPLE 2

5-(4-ethynylbenzoyl)-1,2-dihydro-3H-pyrrolo[1,2-a]pyrrole[1-carboxylic acid

A. Methyl 5-(4-ethynylbenzoyl)-1,2-dihydro-3H-pyrrolo[1,2-a]pyrrole-1-carboxylate.

A solution of methyl 1,2-dihydro-3H-pyrrolo[1,2-a]pyrrole-1-carboxylate (2.50 g, 0.015 mole) in dry xylene (100 ml) containing the acid chloride of 4-ethynylbenzoic acid [4.40 g, 0.026 mole; L. E. Salisbury, J. Org. Chem., 43, 4987 (1978)] was heated at reflux temperature for 12 hours. The solvent was removed in vacuo and the residue was purified by chromatography on alumina (200 g) using hexane/ethyl acetate (95:5) as the eluting solvent to give methyl 5-(4-ethynylbenzoyl)-1,2-dihydro-3H-pyrrolo[1,2-a]pyrrole-1-carboxylate, m.p. 113°-114° C.

U.V. (MeOH) 212, 218 sh, 268, 318 nm (ε 12,600; 12,600; 14,800; 20,000)
I.R. 3311, 1742, 1613 cm$^{-1}$ (CHCl$_3$)
N.M.R. (CDCl$_3$)
  2.43 (m, 2H)
  3.21 (s, 1H)
  3.78 (s, 3H)
  4.13 (t, 1H, J$_1$≃J$_2$≃7 Hz)
  4.56 (m, 2H)
  6.13 (d, 1H, J=4 Hz)
  6.83 (d, 1H, J=4 Hz)
  7.63 (d, 2H, J=8 Hz)
  7.93 (d, 2H, J=8 Hz)
M.S. 293 (M+)
Calcd. for C$_{18}$H$_{15}$NO$_3$: C, 73.70; H, 5.15; N, 4.77. Found: C, 73.79; H, 5.20; N, 4.69.

B. 5-(4-Ethynylbenzoyl)-1,2-dihydro-3H-pyrrolo[1,2-a]pyrrole-1-carboxylic acid

A solution of the above ester (1.70 g, 0.005 mole) in methanol (30 ml) and water (30 ml) containing sodium hydroxide (0.40, g 0.01 mole) was left at room temperature for 2 hours. The methanol was removed in vacuo and the aqueous residue was extracted with ether. The alkaline aqueous phase was cooled to 0° and made acidic to pH 3 with hydrochloric acid. The product was extracted into ethyl acetate, the extract was washed with water, dried over sodium sulfate and evaporated in vacuo to give 5-(4-ethynylbenzoyl)-1,2-dihydro-3H-pyrrolo[1,2-a]pyrrole-1-carboxylic acid, m.p. 16°-162° C.

U.V. 216, 268, 323 nm (ε 11,800; 14,500; 19,100)
I.R. 3311, 1718, 1618 cm$^{-1}$ (KBr)
N.M.R. (CDCl$_3$+DMSO d$_6$)
  2.43 (m, 2H)
  3.35 (s, 1H)
  4.10 (t, 1H, J$_1$≃J$_2$≃7 Hz)
  4.53 (m, 3H)
  6.20 (d, 1H, J=4 Hz)
  6.85 (d, 1H, J=4 Hz)
  7.63 (d, 2H, J=8 Hz)
  7.86 (d, 2H, J=8 Hz)
M.S. 279 (M+)
Calcd. for C$_{17}$H$_{13}$NO$_3$: 0.1H$_2$O: C, 72.62; H, 4.70; N, 4.98. Found: C, 72.51; H, 4.64; N, 4.94.

C. In a similar manner, but substituting the compounds of Formula B wherein Y is lower alkyl, the synthesis of which is described in Preparation 3 hereinabove, for the methyl-1,2-dihydro-3H-pyrrolo[1,2-a]pyrrole-1-carboxylate in the procedures described in paragraphs A and B of this Example, the following compounds of Formula I are obtained:
5-(4-ethynylbenzoyl)-1,2-dihydro-6-methyl-3H-pyrrolo[1,2-a]pyrrole-1-carboxylic acid;
5-(4-ethynylbenzoyl)-1,2-dihydro-6-ethyl-3H-pyrrolo[1,2-a]pyrrole-1-carboxylic acid;
5-(4-ethynylbenzoyl)-1,2-dihydro-6-propyl-3H-pyrrolo[1,2-a]pyrrole-1-carboxylic acid; and
5-(4-ethynylbenzoyl)-1,2-dihydro-6-butyl-3H-pyrrolo[1,2-a]pyrrole-1-carboxylic acid.

D. In a similar manner, but substituting the compounds of Formula B wherein Y is chloro or bromo, the synthesis of which is described in Preparation 4 hereinabove, for the methyl 1,2-dihydro-3H-pyrrolo[1,2-a]pyrrole- 1-carboxylate in the procedures described in paragraphs A and B of this Example, the following compounds of Formula I are obtained:
5-(4-ethynylbenzoyl)-1,2-dihydro-6-chloro-3H-pyrrolo[1,2-a]pyrrole-1-carboxylic acid; and 5-(4-ethynylbenzoyl)-1,2-dihydro-6-bromo-3H-pyrrolo[1,2-a]pyrrole-1-carboxylic acid.

EXAMPLE 3

A solution of 200 mg of 5-(4-vinylbenzoyl)-1,2-dihydro-3H-pyrrolo[1,2-a]pyrrole-1-carboxylic acid in 5 ml of dichloromethane is treated with an excess of ethereal diazomethane, and the reaction mixture is maintained at room temperature for 30 minutes. The solvents and excess reagent are eliminated under reduced pressure and the residue crystallized from ethyl acetate-methanol, to yield methyl 5-(4-vinylbenzoyl)-1,2-dihydro-3H-pyrrolo[1,2-a]pyrrole-1-carboxylate. Likewise but using diazoethane, diazopropane and diazobutane in place of diazomethane there are respectively obtained:
ethyl 5-(4-vinylbenzoyl)-1,2-dihydro-3H-pyrrolo[1,2-a]pyrrole-1-carboxylate;
propyl 5-(4-vinylbenzoyl)-1,2-dihydro-3H-pyrrolo[1,2-a]pyrrole-1-carboxylate; and
butyl 5-(4-vinylbenzoyl)-1,2-dihydro-3H-pyrrolo[1,2-a]pyrrole-1-carboxylate.

In a similar manner, the remaining free acids obtained in Examples 1C, 1D, 2B, 2C and 2D are converated into the corresponding methyl, ethyl, propyl and butyl esters, e.g.,
methyl 5-(4-vinylbenzoyl)-1,2-dihydro-6-methyl-3H-pyrrolo[1,2-a]pyrrole-1-carboxylate;
methyl 5-(4-vinylbenzoyl)-1,2-dihydro-6-butyl-3H-pyrrolo[1,2-a]pyrrole-1-carboxylate;
ethyl 5-(4-vinylbenzoyl)-1,2-dihydro-6-ethyl-3H-pyrrolo[1,2-a]pyrrole-1-carboxylate;
propyl 5-(4-vinylbenzoyl)-1,2-dihydro-6-propyl-3H-pyrrolo[1,2-a]pyrrole-1-carboxylate;
butyl 5-(4-vinylbenzoyl)-1,2-dihydro-6-chloro-3H-pyrrolo[1,2-a]pyrrole-1-carboxylate;
methyl 5-(4-vinylbenzoyl)-1,2-dihydro-6-bromo-3H-pyrrolo[1,2-a]pyrrole-1-carboxylate;
methyl 5-(4-ethynylbenzoyl)-1,2-dihydro-6-bromo-3H-pyrrolo[1,2-a]pyrrole-1-carboxylate;
methyl 5-(4-ethynylbenzoyl)-1,2-dihydro-6-methyl-3H-pyrrolo[1,2-a]pyrrole-1-carboxylate;
ethyl 5-(4-ethynylbenzoyl)-1,2-dihydro-6-ethyl-3H-pyrrolo[1,2-a]pyrrole-1-carboxylate;
propyl 5-(4-ethynylbenzoyl)-1,2-dihydro-6-butyl-3H-pyrrolo[1,2-a]pyrrole-1-carboxylate;
butyl 5-(4-ethynylbenzoyl)-1,2-dihydro-6-methyl-3H-pyrrolo[1,2-a]pyrrole-1-carboxylate;
methyl 5-(4-ethynylbenzoyl)-1,2-dihydro-6-chloro-3H-pyrrolo[1,2-a]pyrrole-1-carboxylate;
butyl 5-(4-ethynylbenzoyl)-1,2-dihydro-6-chloro-3H-pyrrolo[1,2-a]pyrrole-1-carboxylate;
ethyl 5-(4-ethynylbenzoyl)-1,2-dihydro-6-bromo-3H-pyrrolo[1,2-a]pyrrole-1-carboxylate; and
propyl 5-(4-ethynylbenzoyl)-1,2-dihydro-6-bromo-3H-pyrrolo[1,2-a]pyrrole-1-carboxylate.

EXAMPLE 4

A solution of 300 mg of 5-(4-vinylbenzoyl)-1,2-dihydro-3H-pyrrolo[1,2a]pyrrole-1-carboxylic acid in 5 ml of isoamyl alcohol is saturated with hydrogen chloride. After 24 hours, the excess alcohol is distilled off in vacuo and the residue purified by chromatography on alumina, to yield isoamyl 5-(4-vinylbenzoyl)1,2-dihydro-3H-pyrrolo[1,2a]pyrrole-1-carboxylate.

Likewise, other esters, e.g. pentyl, hexyl, octyl, nonyl, docezyl, and the like, are obtained by substituting other alcohols, e.g., pentyl, hexyl, octyl, nonyl, dodecyl alcohol, and the like, for isoamyl alcohol, to give for example:
pentyl 5-(4-vinylbenzoyl)-1,2-dihydro-3H-pyrrolo[1,2-a]pyrrole-1-carboxylate;
hexyl 5-(4-vinylbenzoyl)-1,2-dihydro-3H-pyrrolo[1,2-a]pyrrole-1-carboxylate;
octyl 5-(4-vinylbenzoyl)-1,2-dihydro-3H-pyrrolo[1,2-a]pyrrole-1-carboxylate;
nonyl 5-(4-vinylbenzoyl)-1,2-dihydro-3H-pyrrolo[1,2-a]pyrrole-1-carboxylate; and
dodecyl 5-(4-vinylbenzoyl)-1,2-dihydro-3H-pyrrolo[1,2-a]pyrrole-1-carboxylate.

By the same method, the free acid compounds obtained in Examples 1C, 1D, 2B, 2C and 2D are esterified with the appropriate alcohol, thus obtaining the corresponding esters, e.g.,
isoamyl 5-(4-vinylbenzoyl)-1,2-dihydro-6-methyl-3H-pyrrolo[1,2-a]pyrrole-1-carboxylate;
pentyl 5-(4-vinylbenzoyl)-1,2-dihydro-6-ethyl-3H-pyrrolo[1,2-a]pyrrole-1-carboxylate;
hexyl 5-(4-vinylbenzoyl)-1,2-dihydro-6-propyl-3H-pyrrolo[1,2-a]pyrrole-1-carboxylate;
octyl 5-(4-vinylbenzoyl)-1,2-dihydro-6-butyl-3H-pyrrolo[1,2-a]pyrrole-1-carboxylate;
nonyl 5-(4-vinylbenzoyl)-1,2-dihydro-6-chloro-3H-pyrrolo[1,2-a]pyrrole-1-carboxylate;
dodecyl 5-(4-vinylbenzoyl)-1,2-dihydro-6-bromo-3H-pyrrolo[1,2-a]pyrrole-1-carboxylate;
pentyl 5-(4-ethynylbenzoyl)-1,2-dihydro-6-methyl-3H-pyrrolo[1,2-a]pyrrole-1-carboxylate;
hexyl 5-(4-ethynylbenzoyl)-1,2-dihydro-6-ethyl-3H-pyrrolo[1,2-a]pyrrole-1-carboxylate;
isoamyl 5-(4-ethynylbenzoyl)-1,2-dihydro-6-propyl-3H-pyrrolo[1,2-a]pyrrole-1-carboxylate;
octyl 5-(4-ethynylbenzoyl)-1,2-dihydro-6-butyl-3H-pyrrolo[1,2-a]pyrrole-1-carboxylate;
nonyl 5-(4-ethynylbenzoyl)-1,2-dihydro-6-chloro-3H-pyrrolo[1,2-a]pyrrole-1-carboxylate;
heptyl 5-(4-vinylbenzoyl)-1,2-dihydro-6-ethyl-3H-pyrrolo[1,2-a]pyrrole-1-carboxylate;
heptyl 5-(4-vinylbenzoyl)-1,2-dihydro-6-chloro-3H-pyrrolo[1,2-a]pyrrole-1-carboxylate;
isoamyl 5-(4-vinylbenzoyl)-1,2-dihydro-6-bromo-3H-pyrrolo[1,2-a]pyrrole-1-carboxylate;
pentyl 5-(4-vinylbenzoyl)-1,2-dihydro-6-butyl-3H-pyrrolo[1,2-a]pyrrole-1-carboxylate;
octyl 5-(4-ethynylbenzoyl)-1,2-dihydro-6-methyl-3H-pyrrolo[1,2-a]pyrrole-1-carboxylate; and
dodecyl 5-(4-ethynylbenzoyl)-1,2-dihydro-6-bromo-3H-pyrrolo[1,2-a]pyrrole-1-carboxylate.

EXAMPLE 5

To a solution of 300 mg of 5-(4-vinylbenzoyl)-1,2-dihydro-3H-pyrrolo[1,2-a]pyrrole-1-carboxylic acid in pb 5 ml of methanol is added 1 molar equivalent of sodium hydroxide, in the form of a 0.1 N solution. The solvent is taken up in 2 ml of methanol, followed by precipitation with ether, to yield crude sodium 5-(4-vinylbenzoyl)-1,2-dihydro-3H-pyrrolo[1,2-a]-pyrrole-1-carboxylate which can be crystallized from ethyl acetate-hexane.

Likewise other salts, e.g., ammonium and potassium salts, of 5-(4-vinylbenzoyl)-1,2-dihydro-3H-pyrrolo[1,2-a]pyrrole-1-carboxylic acid or 5-(4-ethynylbenzoyl)-containing compounds are prepared by substituting ammonium hydroxide and potassium hydroxide for sodium hydroxide.

In a similar manner, the 5-substituted-(4-vinylbenzoyl)-1,2-dihydro-3H-pyrrolo[1,2-a]pyrrole-1-carboxylic acid compounds obtained in Examples 1, 2 and 3 can be converted into the corresonding sodium, potasium and ammonium salts.

EXAMPLE 6

To a solution of 175 mg of 5-(4-vinylbenzoyl)-6-chloro-1,2-dihydro-3H-pyrrolo[1,2-a]pyrrole-1-carboxylic acid in 5 ml of methanol is added 1 molar equivalent of potassium hydroxide, in the form of a 0.1N solution, thus yielding a solution containing potassium 5-(4-vinylbenzoyl)-6-chloro-1,2-dihydro-3H-pyrrolo[1,2-a]pyrrole-1-carboxylate. A solution of 40 mg of calcium carbonate dissolved in the minimum amount of 1N hydrochloric acid necessary to effect solution of the calcium carbonate, is buffered with 100 mg of solid ammonium chloride, followed by the further addition of 5 ml of water. The thus obtained buffered calcium solution is then added to the solution of potassium 5-(4-vinylbenzoyl)-6-chloro-1,2-dihydro-3H-pyrrolo[1,2-a]pyrrole-1-carboxylate and the precipitate which forms is collected by filtration, washed with water and air dried to yield calcium 5-(4-vinylbenzoyl)-6-chloro-1,2-dihydro-3H-pyrrolo[1,2-a]-pyrrole-1-carboxylate.

Likewise, magnesium 5-(4-vinylbenzoyl)-6-chloro-1,2-dihydro-3H-pyrrolo[1,2-a]pyrrole-1-carboxylate is prepared by substituting magnesium carbonate for calcium carbonate.

Similarly, by substituting other carboxylic acids of Examples 1, 2 and 3 for 5-(4-vinylbenzoyl)-6-chloro-1,2-dihydro-3H-pyrrolo[1,2-a]-pyrrole-1-carboxylic acid there are obtained the corresponding calcium and magnesium salts.

EXAMPLE 7

To a solution of 200 mg of 5-(4-vinylbenzoyl)-6-chloro-1,2-dihydro-3H-pyrrolo[1,2-a]pyrrole-1-carboxylic acid in 5 ml of methanol is added 1 molar equivalent of potassium hydroxide in the form of a 0.1N solution. The solvent is stripped and the residue is dissolved in 5 ml of water. The thus obtained aqueous solution of potassium 5-(4-vinylbenzoyl)-6-chloro-1,2-dihydro-3H-pyrrolo[1,2-a]pyrrole-1-carboxylate is added to a solution of 150 mg of cupric nitrate trihydrate in 5 ml of water. The formed precipitate is collected, washed with water and air dried, thus obtaining copper 5-p-chlorobenzoyl-6-chloro-1,2-dihydro-3H-pyrrolo[1,2-a]-pyrrole-1-carboxylate.

In a similar manner the free acid compounds obtained in Examples 1, 2 and 3 can be converted into the corresponding copper salts.

EXAMPLE 8

A solution of 200 mg of 5-(4-vinylbenzoyl)-6-chloro-1,2-dihydro-3H-pyrrolo[1,2-a]pyrrole-1-carboxylic acid in 15 ml of hot benzene is treated with 60 mg of isopropylamine. The solution is allowed to cool to room temperature and the product filtered off, washed with ether and dried to yield the isopropylamine salt of 5-(4-vinylbenzoyl)-6-chloro-1,2-dihydro-3H-pyrrolo[1,2-a]-pyrrole-1-carboxylic acid.

Likewise other amine salts, e.g., diethylamine, ethanolamine, piperidine, tromethamine, choline and caffeine salts of 5-(4-vinylbenzoyl)-6-chloro-1,2-dihydro-3H-pyrrolo[1,2-a]pyrrole-1-carboxylic acid or the 5-(4-ethynylbenzoyl) containing compounds are prepared by substituting each of the respective amines for isopropylamine.

In similar manner the free acid compounds obtained in Examples 1, 2 and 3 can be converted into the corresponding isopropylamine, diethylamine, ethanolamine, piperidine, tromethanmine, choline and caffeine salts.

EXAMPLE 9

| Ingredients | Quantity per tablet, mgs. |
| --- | --- |
| 5-(4-vinylbenzoyl)-1,2-dihydro-3H—pyrrolo[1,2-a]pyrrole-1-carboxylic acid | 25 |
| cornstarch | 20 |
| lactose, spray-dried | 153 |
| magnesium stearate | 2 |

The above ingredients are thoroughly mixed and pressed into single scored tablets.

Other 1-carboxylic acids or their esters or salts of Examples 2 and 3 or 6-9 can be substituted for the compound of the above composition.

EXAMPLE 10

| Ingredients | Quantity per capsule, mgs. |
| --- | --- |
| 5-(4-vinylbenzoyl)-1,2-dihydro-3H—pyrrolo[1,2-a]pyrrole-1-carboxylic acid | 100 |
| lactose | 148 |
| magnesium stearate | 2 |

The above ingredients are mixed and introduced into a hard-shell gelatin capsule.

Other free acids, their salts or esters of Examples 1-3 can be substituted for the compound of the above composition.

EXAMPLE 11

| Ingredients | Quantity per capsule, mgs. |
| --- | --- |
| 5-(4-vinylbenzoyl)-1,2-dihydro-3H—pyrrolo[1,2-a]pyrrole-1-carboxylic acid | 200 |
| cornstarch | 50 |
| lactose | 145 |
| magnesium stearate | 5 |

The above ingredients are mixed intimately and pressed into single scored tablets.

EXAMPLE 12

| Ingredients | Quantity per capsule, mgs. |
| --- | --- |
| methyl 5-(4-vinylbenzoyl)-1,2-dihydro-3H—pyrrolo[1,2-a]pyrrole-1-carboxylic acid | 108 |
| lactose | 15 |
| cornstarch | 25 |
| magnesium stearate | 2 |

The above ingredients are mixed and introduced into a hard-shell gelatin capsule.

EXAMPLE 13

| Ingredients | Quantity per capsule, mgs. |
| --- | --- |
| calcium 5-(4-vinylbenzoyl)-1,2- | 115 |

-continued

| Ingredients | Quantity per capsule, mgs. |
|---|---|
| dihydro-3H—pyrrolo[1,2-a]pyrrole-1-carboxylic acid | |
| lactose | 93 |
| cornstarch | 40 |
| magnesium stearate | 2 |

The above ingredients are mixed and introduced into a hard-shell gelatin capsule.

EXAMPLE 14

| Ingredients | Quantity per capsule, mgs. |
|---|---|
| 5-(4-vinylbenzoyl)-1,2-dihydro-3H—pyrrolo[1,2-a]pyrrole-1-carboxylic acid | 100 |
| sucrose | 100 |

The above ingredients are thoroughly mixed and processed into aingle scored tablets.

EXAMPLE 15

| Ingredients | Quantity per capsule, mgs. |
|---|---|
| isoamyl 5-(4-vinylbenzoyl)-1,2-dihydro-3H—pyrrolo[1,2-a]pyrrole-1-carboxylic acid | 254 |
| cornstarch | 50 |
| lactose | 190 |
| magnesium stearate | 6 |

The above ingredients are mixed intimately and pressed into single scored tablets.

EXAMPLE 16

| Ingredients | Quantity per capsule, mgs. |
|---|---|
| 5-(4-vinylbenzoyl)-1,2-dihydro-3H—pyrrolo[1,2-a]pyrrole-1-carboxylic acid | 100 |
| lactose | 148 |
| dextrose | 2 |

The above ingredients are mixed and introduced into a hard-shell gelatin capsule.

EXAMPLE 17

| Ingredients | Quantity per capsule, mgs. |
|---|---|
| methyl 5-(4-vinylbenzoyl)-1,2-dihydro-3H—pyrrolo[1,2-a]pyrrole-1-carboxylic acid | 150 |
| lactose | 92 |

The above ingredients are mixed and introduced into a hard-shell gelatin capsule.

EXAMPLE 18

An injectable preparation buffered to a pH of 7 is prepared having the following composition:

| | |
|---|---|
| 5-(4-vinylbenzoyl)-1,2-dihydro-3H—pyrrolo[1,2-a]pyrrole-1-carboxylic acid | 0.2 g |
| $K_2HPO_4$ buffer (0.4 M solution) | 2 ml. |
| KOH (1 N) q.s. to | pH 7 |
| water (distilled sterile) q.s. to | 20 ml. |

Other 1-carboxylic acids of this invention may be substituted for the compound of the above composition.

EXAMPLE 19

A suppositiory totaling 2.5 grams is prepared having the following composition:

| | |
|---|---|
| 5-(4-vinylbenzoyl)-1,2-dihydro-3H—pyrrolo[1,2-a]pyrrole-1-carboxylic acid | 25 mg |
| Witepsol H—15 (triglycerides of saturated vegetable fatty acids; a product of Riches-Nelson, Inc., New York, N.Y.) | balance |

Other carboxylic acids of this invention may be substituted for the compound of the above composition.

EXAMPLE 21

An oral suspension is prepared having the following composition:

| | |
|---|---|
| 5-(4-vinylbenzoyl)-1,2-dihydro-3H—pyrrolo[1 2-a]pyrrole-1-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water q.s. to | 100 ml. |

Other carboxylic acids of this invention may be substituted for the compound of the above composition.

EXAMPLES 21-22

Powdered top dressings for veterinary use are prepared having the following compositions:

| | Ex. 22 | Ex. 23 |
|---|---|---|
| 5-(4-vinylbenzoyl)-1,2-dihydro-3H—pyrrolo[1,2-a]pyrrole-1-carboxylic acid | 0.1 g. | 1.2 g. |
| sucrose | 5.7 g. | 3.7 g. |
| polyvinyl pyrrolidone | 0.3 g. | 0.3 g. |

Other 1-carboxylic acids of this invention may be substituted for the compound of the composition of Example 15 or 16.

EXAMPLE 23

Screening test for anti-inflammatory activity

The oral anti-inflammatory activity is determined utilizing carrageenin induced paw inflammation in the rat in accordance with the method of Winter et al (Pro Soc Exp Biol Med, 111:544–547, 1962).

Materials and Methods

Female rats weighing 80–90 grams are used. The test materials are given at hour 0 orally by gavage in 1 ml aqueous vehicle. At hour 1, 0.05 ml of a 1% solution (in 0.9% NaCl) of carrageenin is injected into the right hind paw. This injection causes an inflammation of the paw. The rats are sacrificed at hour 4, at which time both hind paws are removed and weighed separately.

End Point

The % increase in paw size is calculated as follows:

$$\frac{\text{Wt. of Right Paw} - \text{Wt. of Left Paw}}{\text{Wt. of Left Paw}} \times 100$$

The smaller the % increase in paw size, the lesser the degree of inflammation and the greater the anti-inflammatory activity.

Compounds of this invention show anti-inflammatory activity in this test.

EXAMPLE 24

Screening Test for analgetic activity

The oral analgetic activity potential is determined utilizing the mouse analgetic (anti-writhing) assay in accordance with the method of Hendershot and Forsaith (J Pharmacol Exp Ther 125:237–240, 1959).

Materials and Methods

The test material is administered orally by gavage in an aqueous vehicle at time 0 to 18–20 gram male Swiss-Webster mice. Twenty minutes later 0.25 ml of a 0.02% solution of phenylquinone is injected intraperitoneally. This solution induces writhing.

End point

The total number of mice that writhe and the average numbe of writhes per mouse indicates the activity of the compound tested; the fewer writhes per mouse indicates a greater activity.

Compounds of this invention show analgetic activity in this assay.

What we claim is:

1. A compound selected from the group of those represented by the formula

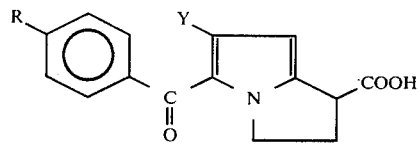

and the pharmaceutically acceptable, non-toxic alkyl esters having from 1 to 12 carbon atoms and the pharmaceutically acceptable salts thereof wherein
R is vinyl, and
Y is hydrogen, a lower alkyl having from 1 to 6 carbon atoms, chloro or bromo.

2. The compound of claim 1 wherein Y is hydrogen, namely, 5-(4-vinylbenzoyl)-1,2-dihydro-3H-pyrrolo-[1,2-a]-pyrrole-1-carboxylic acid and the pharmaceutically acceptable, non-toxic alkyl esters having from 1 to 12 carbon atoms and the pharmaceutically acceptable salts thereof.

3. The compound of claim 1 wherein Y is lower alkyl having 1 to 6 carbon atoms, chloro or bromo.

4. A pharmaceutical composition comprising a pharmaceutically acceptable excipient and at least one compound represented by the formula:

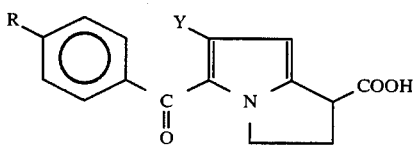

and the pharmaceutically acceptable, non-toxic alkyl esters having from 1 to 12 carbon atoms and the pharmaceutically acceptable salts thereof wherein
R is vinyl, and
Y is hydrogen, a lower alkyl having from 1 to 6 carbon atoms, chloro or bromo.

5. A method of treating inflammation and pain in mammals which comprises administering to a mammal suffering therefrom a therapeutically effective amount of a compound of claim 1 alone or in admixture with a pharmaceutically acceptable excipient.

* * * * *